(12) United States Patent
Morrison et al.

(10) Patent No.: US 11,244,767 B1
(45) Date of Patent: Feb. 8, 2022

(54) PATIENT PAYMENT SYSTEM AND METHOD FOR THE REAL-TIME PREVENTION OF HEALTHCARE CLAIM ADJUDICATION CIRCUMVENTION IN ALL 100% COPAY SITUATIONS

(71) Applicants: Richard James Morrison, Little Rock, AR (US); Walter James Morrison, Hot Springs Village, AR (US)

(72) Inventors: Richard James Morrison, Little Rock, AR (US); Walter James Morrison, Hot Springs Village, AR (US)

(*) Notice: Subject to any disclaimer, the term of this patent is extended or adjusted under 35 U.S.C. 154(b) by 559 days.

(21) Appl. No.: 16/159,024

(22) Filed: Oct. 12, 2018

(51) Int. Cl.
| | |
|---|---|
| *G06Q 30/04* | (2012.01) |
| *G16H 80/00* | (2018.01) |
| *G16H 10/60* | (2018.01) |
| *G06Q 20/04* | (2012.01) |
| *G06Q 20/14* | (2012.01) |

(Continued)

(52) U.S. Cl.
CPC ........... *G16H 80/00* (2018.01); *G06Q 20/027* (2013.01); *G06Q 20/047* (2020.05); *G06Q 20/10* (2013.01); *G06Q 20/102* (2013.01); *G06Q 20/14* (2013.01); *G06Q 30/04* (2013.01); *G16H 10/60* (2018.01); *G06Q 40/08* (2013.01)

(58) Field of Classification Search
CPC .... G06Q 20/047; G06Q 20/027; G06Q 20/10; G06Q 20/102; G06Q 20/14; G06Q 30/04; G06Q 40/08; G16H 80/00; G16H 10/60
USPC ...................................................... 705/3–44
See application file for complete search history.

(56) References Cited

U.S. PATENT DOCUMENTS

| 6,519,571 B1* | 2/2003 | Guheen | G06Q 30/02 |
| | | | 705/14.66 |
| 7,774,273 B2* | 8/2010 | Neal | G06Q 20/342 |
| | | | 705/39 |

(Continued)

OTHER PUBLICATIONS

"HealthPay24(r) Partners with CardConnect to Deliver the latest in Patient Payment Innovation", Accession No. 5023800813, Plus Company Updates Aug. 30. (Year: 2017).*

(Continued)

*Primary Examiner* — Frantzy Poinvil
(74) *Attorney, Agent, or Firm* — Shlesinger, Arkwright & Garvey LLP

(57) ABSTRACT

Computerized method requiring claim adjudication to receive patient payment for a product or service provided by a healthcare provider to a patient with full financial responsibility, including receiving a patient claim; re-pricing the claim, automatically initiating a real-time payment authorization request through a payment gateway; receiving a real-time notification that the patient's funding source has verified funds availability, with the funds to be deposited in a designated account for subsequent provider payment; sending the healthcare provider the copay and plan pay pricing edits; and concurrently, sending the patient a payment e-receipt electronically, indicating the total amount due and the amount debited from the patient's funding source, the plan payment, with any difference the copay to be paid directly to the provider. Automatic real-time patient audit enabling payment e-receipts indicate claim adjudications and claim reversals as well as adjudicated copay and plan pay amounts, with the plan payment eliminating adjudication circumvention.

3 Claims, 4 Drawing Sheets

(51) Int. Cl.
*G06Q 20/10* (2012.01)
*G06Q 20/02* (2012.01)
*G06Q 40/08* (2012.01)

(56) References Cited

U.S. PATENT DOCUMENTS

| | | | |
|---|---|---|---|
| 8,510,124 | B2 | 8/2013 | Gowdy et al. |
| 8,526,573 | B2 | 9/2013 | Ferro, Jr. |
| 8,645,162 | B2 | 2/2014 | Boerger et al. |
| 8,682,697 | B1 | 3/2014 | Harris, Sr. |
| 9,082,119 | B2 * | 7/2015 | Ortiz .................. G06Q 20/322 |
| 10,046,228 | B2 * | 8/2018 | Tran ...................... H04L 9/3236 |
| 10,255,996 | B2 * | 4/2019 | Ivanoff ................. G16H 50/20 |
| 10,719,581 | B2 * | 7/2020 | Lacy ..................... G06Q 30/04 |
| 2004/0064386 | A1 | 4/2004 | Goguen |
| 2009/0271220 | A1 | 10/2009 | Radoccia |
| 2011/0119082 | A1 | 5/2011 | Drucker et al. |
| 2011/0161109 | A1 | 6/2011 | Pinsonneault |
| 2012/0053958 | A1 * | 3/2012 | Marshall ............... G06Q 30/02 705/2 |
| 2013/0268437 | A1 * | 10/2013 | Desai .................... G06Q 20/08 705/41 |
| 2013/0339232 | A1 * | 12/2013 | Desai ....................... G06F 8/65 705/41 |
| 2014/0019155 | A1 | 1/2014 | Smith |
| 2014/0142964 | A1 | 5/2014 | Lang et al. |
| 2014/0244280 | A1 | 8/2014 | Fitz |
| 2015/0193750 | A1 * | 7/2015 | Ivanoff .................. G16H 50/20 705/40 |
| 2015/0206262 | A1 | 7/2015 | Pinsonneault |
| 2016/0103965 | A1 * | 4/2016 | Ivanoff ................ G06Q 20/102 705/2 |
| 2016/0210626 | A1 * | 7/2016 | Ortiz .................... G06Q 20/023 |
| 2016/0253651 | A1 * | 9/2016 | Park ......................... G07F 9/023 705/39 |
| 2016/0342758 | A1 * | 11/2016 | Ivanoff .................. G06Q 20/14 |
| 2018/0253727 | A1 * | 9/2018 | Ortiz .................... G06Q 20/325 |

OTHER PUBLICATIONS

"MintHealth: Empowering Patients to Take Control of their Health and Data via Blockchain Technology", PR Newswire, New York Oct. 26. (Year: 2017).*

* cited by examiner

PATIENT PAYMENT SYSTEM AND METHOD FOR THE REAL-TIME PREVENTION OF HEALTHCARE CLAIM ADJUDICATION CIRCUMVENTION IN ALL 100% COPAY SITUATIONS

RELATED APPLICATION

This is a nonprovisional application claiming the benefit of Provisional Application Ser. No. 62/572,239, filed Oct. 13, 2017, incorporated herein by reference.

FIELD OF THE INVENTION

The present invention generally relates to that segment of the healthcare economy in which patients have an unknown financial responsibility, such as healthcare plans and programs under which patients, at some point, have full financial responsibility for the cost of products and services received. Examples of the preceding include 100% patient copayment (copay) programs and plans such as cash discount programs, and all High Deductible Health Plans (HDHPs), including all Consumer Driven Health Plans (CDHPs), such as Health Savings Accounts (HSAs), Health Reimbursement Accounts (HRAs), Flexible Spending Accounts (FSAs), and Medical Savings Accounts (MSAs), before patients have met their deductible.

BACKGROUND OF THE INVENTION

When health care providers receive pricing edit responses from healthcare claims processors that indicate patients are financially responsible for the entire cost of their services or products (100% copay), health care providers recognize the opportunity to charge and collect more than the pre-negotiated, discounted reimbursement rates under the applicable health plan or program without detection at the point of service, with detection at a later date highly improbable. Discounts, that providers have felt forced to accept under managed care plans, have spiraled down over time and are now well below their preferred margins. This has led health care providers to subsidize those discounts by charging patients more than the health care provider's contracted rates when patients are financially responsible for the entire cost of their services or products (100% copay). Health care providers can be expected to continue this practice as long as there continues to be very little risk of being caught; and existing penalties, if any, have not eliminated this problem.

Account-based health plans, commonly referred to as Consumer Driven Health Plans (CDHPs), are the fastest growing segment of healthcare coverage; and this trend is expected to continue for the foreseeable future. The cost to provide traditional health insurance to an aging population coupled with governmental regulation/health reform is expected to cause traditional health insurance premiums to continue to increase at an alarming rate. Add a struggling economy, and an ideal scenario is created for the explosive growth of CDHPs. In order to secure lower premiums, almost half of the market has already shifted to HDHPs with a deductible that is just a little under that required to qualify for a Health Savings Account (HSA). The premiums for CDHPs tend to be considerably less than traditional health insurance; and as traditional health insurance premiums continue to climb, the healthier population, that historically has subsidized the sicker population under traditional insurance programs, will gravitate to a CDHP in order to lower their total cost of health care. This will generate a subsidy loss and traditional health insurance premiums will increase even more. This adverse selection cycle is expected to continue over time with the net effect of a higher CDHP population than traditional insurance. This trend is expected to continue, if not accelerate, in the foreseeable future.

CDHPs are the only plans proven to "bend the cost curve". Mandates, subsidies, wellness incentives, and excise tax on "Cadillac" plans, could all push more people into CDHPs. As the Affordable Care Act, or any foreseeable replacement, transitions patients without insurance to adopting High Deductible Health Plans (HDHPs), which includes CDHPs, because of their greater affordability, health care providers' "cash cow targets" will be transitioning from patients without insurance to those patients utilizing insurance products that have a deductible attached. Unfortunately, this major transition places patients in the vulnerable position of easily being treated as "cash cows" by health care providers who can circumvent the claim adjudication process to secure their preferred margins without detection at the point of service. Consequently, patients are vulnerable to being charged more than contracted, claim adjudicated rates without their knowledge or consent.

Currently, in 100% copay situations, there are no published statistics on the frequency of claim adjudication circumvention. There is no way to track, measure, or prevent its occurrence at the point of service because neither patients, healthcare claims processors nor health Plans know if the health care providers have circumvented the claim adjudication process to 1) collect higher reimbursement fees, and/or 2) avoid paying fees to a healthcare claims processor which is commonly associated with cash discount programs for providing "patient steerage" to the health care provider when they provide a product or service, or 3) for some other reason (drug incompatibilities, prices higher than patients are willing to pay, etc.). Under cash discount programs, the vulnerability is greater because health care providers may not even submit claims when such programs are identified upfront; or they may reverse a submitted claim to avoid paying a fee that is assessed by healthcare claims processors for providing "patient steerage" to the health care provider. Under Consumer Driven Health Plans, approximately ninety percent (90%) of plan members never meet their deductible and under traditional High Deductible Health Plans (HDHPs), approximately fifty percent (50%) of plan members never meet their deductible. This further reduces the potential for health care providers being caught; because before deductibles are met, patients in these plans experience the same vulnerability as they would under cash discount programs. The difference between HDHPs/CDHPs and cash discount cards is that HDHPs/CDHPs have a deductible that, once met, automatically converts to a cost-sharing arrangement with the health plan and this eliminates the claim circumvention problem.

The market place problem the present invention addresses and eliminates is the ability of health care providers to "game" the system by circumventing the adjudication (price determination) process by either failing to submit claims or reversing submitted claims when they realize the responsibility for payment is entirely that of patients. This enables health care providers to 1) charge "what the market will bear" rather than the pre-negotiated, discounted prices as specified in the healthcare claims processor's pricing edits, and/or 2) avoid paying a fee that is assessed by the healthcare claims processor for providing "patient steerage" to the health care provider providing a product or service under a cash discount program. At the point of service, the health care provider's actions are undetectable because the healthcare claims processor is not aware that claims have not been submitted for adjudication, and if claims are reversed, the reason for the providers' reversals are not known. For example, there could be a logical, clinical reason for reversals. Also, without the present invention, patients have no way of knowing if a provider reversed a claim, thus eliminating the posting of the patient's product or service to the patient's claims history. Therefore, in all 100% copay situations, patients and the healthcare claims processors are completely vulnerable to health care providers unilaterally circumventing the claim adjudication process without their knowledge or consent and charging "what the market will bear".

Providers have been confronted with ever decreasing reimbursement rates from health insurance/cash discount program entities; and patients who are totally responsible for providers' charges (100% copay) provide an opportunity for providers to charge their preferred rates rather than the health plan/program discounted rates they have been "forced" to accept. Detection of this practice is highly unlikely, and penalties, if any, are minimal in the unlikely event they are caught. Therefore, providers can be expected to consider the relative "risk" of being detected against the "reward" of being able to charge their desired, higher price. When it is easy to exploit a system for financial gain, with very little chance of being caught, and limited to no penalties, it is logical to conclude that a significant percentage of providers will take advantage of the opportunity. Circumventing the claims adjudication process to: 1) charge a higher fee from a patient under 100% copay situations, and/or 2) avoid paying a fee that is assessed by the healthcare claims processor for providing "patient steerage" to the health care provider providing a product or service under a cash discount program may not be consistent with the terms of health care providers' contracts; but the repercussions, if any, in the unlikely event a health care provider is caught, has not eliminated the problem.

When providers circumvent the adjudication process, pricing is only one of six significant problems that are experienced under High Deductible Health Plans (HDHPs) and Consumer Directed Health Plans (CDHPs), the fastest growing segment of health care coverage—growing annually at double digits. The six (6) problems that can be experienced when the claims adjudication process is circumvented are:

1. Patients paying more than the contracted, discount rates for their products and services.
2. Claims not being counted toward patients' deductibles (when applicable).
3. Deductibles, if applicable, not being tracked at the point of service. This means that, if patients would hit their deductible with the service or product then being provided, they would not receive the benefit of a reduction in their financial responsibility at that time, with their third party (such as a health plan, etc.) picking up the difference.
4. Patients not receiving concurrent Drug Utilization Review (DUR) on all prescriptions, thereby making them susceptible to drug therapy related problems that otherwise could have been avoided. Concurrent DUR is provided via healthcare claims processors' computerized programs that, before prescriptions are dispensed, electronically alert pharmacists to drug interactions, duplicate therapies, and other potential drug therapy related problems caused by taking two or more prescription drugs. Through DUR, the cost of therapy is controlled and becomes cost-effective because it reduces the need for other medical services, such as hospitalizations, nursing home admissions, and additional physician visits. It also decreases the potential for meeting patient deductibles, thereby minimizing the underwriting risk. Obviously, circumventing the adjudication process increases patients' risk for drug therapy related problems. There are comparable medical care issues.
5. Data required for accurate actuarial and clinical analysis, risk prediction, projected outcomes and optimal provider compensation under pay-for-performance (P4P), or value-based purchasing models are incomplete. Consequently, any results derived from available data would be inaccurate.
6. Healthcare claims processors lose the revenue that would be received by processing the circumvented claims.

The significance of the problem in the pharmacy benefits sector alone is illustrated by the fact that it is not uncommon for cash discount programs to experience claim reversal rates ranging from twenty percent (20%) to fifty percent (50%), with those reversal rates ranging from four (4) to ten (10) times that experienced under traditional, fully funded pharmacy benefit plans when patients' (cost-sharing) copays alone are approximately the same amount as the average prescription cost under cash discount programs. Therefore, the cost of the products or services being provided is not responsible for the difference in reversal rates. Under traditional prescription drug s that utilize a cost-sharing copay structure, provider self-serving claim circumvention is not possible because plans (insurers) are responsible for a share of the cost and claim submission is required in order to receive the plan share of the adjudicated cost of the product or service for full payment.

The bottom line is that because of cost differentials in traditional health plans and various types of High Deductible Health Plans (HDHPs), including all Consumer Driven Health Plans (CDHPs), HDHPs/CDHPs can be expected to grow by double digits annually; and this growth increases the probability for the identified risks/problems to be experienced by increasingly more patients.

Aside from the pricing issue, the problem of a health care provider reversing a previously submitted claim under HDHPs/CDHPs is that the problems identified in items 2-6, above, continue to be experienced even though the health care provider may have assessed the patient the correct pricing. Securing a higher profit margin is not always the sole reason for circumventing the adjudication process. Health care providers may opt to circumvent the adjudication process under cash discount programs to avoid being assessed a fee by the healthcare claims processor for adjudicating the claim, a common practice in that market. Therefore, preventing health care providers from circumventing the adjudication process not only benefits patients, but also healthcare claims processors because, by forcing compliance with their health care provider network agreements, they increase their revenue.

Under HDHPs/CDHPs, patients may receive retrospective, hardcopy Explanation of Benefits (EOBs) that enable them to identify claims that have been adjudicated and the amount of their financial responsibility for the products/services that have been provided. Patients could use the EOB to identify a received product or service that is missing from the FOB, thus identifying those instances when adjudication circumvention has taken place; however, the vast majority of patients do not review EOBs for what is missing, but rather for what has been included. Likewise, some healthcare entities may make available their retrospective EOBs online by providing an online portal to provide patients the ability to log in and identify the claims that have been submitted for adjudication and the amount for which they were financially responsible. Patients typically assume available EOBs are correct and rarely review them for what is missing, making a retrospective EOB review process ineffective in identifying or reducing claim adjudication circumvention. In order to be effective, a majority of patients would need to review EOBs for what is missing as opposed to the information provided, by retaining accurate records of all products and services received in order to compare their retained records to their EOBs. Even if the majority of patients maintained such records and diligently made comparisons, it would still be a retrospective process that doesn't prohibit claim adjudication circumvention at the point of service and would require costly corrective action. Obviously, the corrective action would be retrospective and generate problems for both patients and plans. Experience indicates retrospective approaches to the problem have not been effective in eliminating the claim adjudication circumvention problem.

There are several problems with a retrospective approach: 1) the process is retrospective; therefore, corrective action can only take place at a later date in the unlikely event claim adjudication circumvention is discovered by a patient; 2) at the point of service, health care providers have the opportunity to circumvent the adjudication process and charge "what the market will bear" without detection; 3) there is no significant deterrent for health care providers "gaming" the system since there is very little chance of being caught because of the low percentage of patients that routinely use the EOBs to verify that all of their claims have been adjudicated and the correct amount was paid; 4) there is no way for plans or healthcare claims processors to track, measure, or prevent the occurrence of claim adjudication circumvention because neither patients, healthcare claims processors, nor health plans know when health care providers have either failed to submit claims for adjudication or reversed claims to collect higher reimbursement rates or for some appropriate reason (clinical, etc.); 5) the process relies solely on "paranoid" or extremely "cost sensitive" patients to a) retain complete records of all products/services received; b) make a conscious effort to track the cumulative balance of their healthcare expenses; and c) go through a frustrating appeals process in order for the circumvented claims to be counted toward the patient's deductible, and if having met the deductible, secure reimbursement from their health plan; 6) health plans would then need to deduct the over-charged amounts from future health care provider payments until health plans have recovered the excess payments that health care providers have collected from patients. For the retrospective process to be effective, all patients have to assume responsibility for a retrospective audit and retain all of their receipts to document evidence of their assertions.

Experience indicates that the vast majority of patients simply assume that claims have been submitted and all charges were correct. As previously noted, major pharmacy benefit management firms experience reversal rates ranging from twenty percent (20%) to fifty percent (50%) under cash discount programs which astonished those Pharmacy Benefit Management firms from whom reversal rates were requested and received. These reversal rates range from four (4) to ten (10) times that experienced under traditional, fully funded, pharmacy benefit plans when patients' (cost-sharing) copays are approximately the same amount as the average prescription cost under the cash discount programs. Therefore, the cost of the products or services being provided is not responsible for the difference in reversal rates. Under traditional prescription drug plans that utilize a cost-sharing copay structure, claim circumvention is not possible because plans (insurers) are responsible for a share of the cost.

When patients use an identification card that discloses their use of a cash discount program, health care providers are made aware that patients bear the full financial responsibility for the cost of the products or services being sought. At that point, health care providers are able to exercise a unilateral decision to NOT submit a claim in order to secure their preferred higher prices than previously negotiated and agreed upon discounted prices. The preceding is accomplished without the patients', healthcare claim processors', or health plans' (programs') consent or knowledge. Health care providers' actions to circumvent the claim adjudication process for the purpose of securing higher reimbursements are undetectable because healthcare claims processors and health plans (programs) have no record of claims and no knowledge that patients received either products or services. At the point of service, patients are unaware that claims have not been submitted and furthermore, patients have no knowledge of the correct, contractual fees owed.

Additionally, when health care providers submit claims online under healthcare benefit plans and cash discount programs in which patients bear the full financial responsibility for the cost of the products or services at some point during their plan year, providers receive pricing information (edits) that specifies the amounts they should collect from patients and the amounts third parties will pay after applicable deductibles, if any, have been met. Based upon copay edits received from healthcare claims processors, health care providers are made aware on those occasions when patients have full financial responsibility. At that point, in order to secure a price higher than the healthcare processors' adjudicated discounted price indicated in the edits, health care providers are able to exercise a unilateral decision to reverse the claim and disregard previously provided pricing edits that indicate the amount health care providers should collect from the patient. The preceding is accomplished without the patients', healthcare claim processors', or health plans' knowledge or consent because, at the time claims are submitted, healthcare claims processors cannot confirm the reason (appropriate or inappropriate) that claims were submitted and reversed; and patients have no knowledge of the correct, adjudicated fees that they owe for products or services.

Also, health care providers may identify patients as participating in High Deductible Health Plans, including Consumer Driven Health Plans, at the beginning of a plan year and elect to circumvent the claims adjudication process entirely by not submitting claims online and charging patients higher fees than their contracted, adjudicated rates. Again, health care providers' actions are undetectable because healthcare claims processors have no knowledge claims were not submitted; and patients have no knowledge 1) that the claims adjudication process has been circumvented, or 2) of the contractual fees that they actually owe for their products and services. Therefore, in all 100% copay situations, patients are completely vulnerable to health care providers circumventing the claim adjudication process and charging "what the market will bear" without their knowledge or consent.

When health care providers circumvent the claim adjudication process without the patients', healthcare claims processors', or health plans' knowledge or consent, the following problems are experienced: 1) patients paying more than the plan or program negotiated contract discount rates for their products and services; 2) claims not being counted toward patients' deductibles (when applicable); 3) deductibles, if applicable, not being tracked at the point of service to identify when deductibles have been met; 4) therapy related problems such as duplicate therapies, drug interactions, etc. not being detected and avoided; 5) data required for accurate actuarial and clinical analysis, risk prediction, projected outcomes and optimal provider compensation under pay-for-performance (P4P), or value-based purchasing models are incomplete and inaccurate; and 6) healthcare claims processors lose the revenue that would be received by processing the circumvented claims.

In addition to addressing financial and claims history issues by enabling patients to pay their health care providers' adjudicated charges via the healthcare claims processor and audit the actions of health care providers regarding a claim reversal or voided claim (hereafter, referred to as "claim reversal"), if any, typically in real-time, but at a time determined by the healthcare claims processor, the present invention also may have applicability when health care providers utilize a healthcare claims processor for the purpose of pre-adjudicating or providing an "estimate" of patients' financial responsibility. In such instances, health care providers may opt to charge and collect more than the healthcare claims processor's estimated calculation of the patient's financial responsibility in an effort to eliminate the potential of not being able to collect the ultimately determined amount of the patient's financial responsibility if it exceeds the estimated amount. Health care providers recognize the opportunity to charge and collect more than the discounted, pre-negotiated reimbursement rates without detection in all 100% copay situations. In this scenario and in the highly unlikely event patients discover they have paid more than their final determination of the patient's financial responsibility, patients must seek reimbursement from their health plan, which is a frustrating experience for patients and an expensive process for health plans. This leaves health plans the need to deduct the over-charged amounts from future payments until health plans have recovered the excess payments that health care providers have collected from patients. Health care providers engage in this practice because experience indicates that, once patients leave the point of service without paying for the service or product received, providers are at-risk of not being able to collect the balances owed. Furthermore, health care providers often write-off unpaid balances because pursuing the collection of unpaid balances often cost more than the unpaid balances owed by patients.

OBJECTS AND SUMMARY OF THE INVENTION

The present invention enables patients and healthcare claims processors to prevent health care providers from circumventing the claim adjudication process that can result in six significant problems mentioned above.

The present invention transfers control of the claim submission and reversal decisions from the healthcare provider to the patient because it precludes the healthcare provider self-serving claim circumvention and claim reversal actions.

The objects of the present invention are to eliminate healthcare claim adjudication circumvention and the six noted problems experienced when claims are not adjudicated, including the elimination of inappropriate health care provider excess charges and related problems, enhance the quality of patient care by eliminating clinical problems, increase appropriate healthcare claims processor net revenue under cash discount card programs, and facilitate accurate actuarial and clinical analysis, risk prediction, projected outcomes and optimal provider compensation under pay-for-performance (P4P), or value-based purchasing models.

The present invention eliminates the preceding problems by eliminating claim adjudication circumvention via real-time healthcare claims processor initiated payments to health care providers during the adjudication process on behalf of patients for the products and services received when the patient's previously provided source of funding for their payments is adequate for such payment. A patient payment e-receipt notification not only verifies claim submission and adjudication, but also indicates the adjudicated price to be paid for the service/product received and the amount to be paid, if any, from the patient's source of funding based upon the availability of funds from the patient's registered funding source and/or the healthcare plan design.

The payment e-receipt message notification is typically a real-time process, but the healthcare claims processor determines the timing. There are three payment possibilities: 1) full payment, 2) partial payment, and 3) no payment. The payment e-receipt: 1) assures the patient that their claim has been submitted and adjudicated, 2) indicates the total amount that is to be paid, 3) indicates the amount, if any, being funded via their previously provided source of funding for such payments (represented to the health care provider as the "plan" pay edit), and 4) indicates the amount to be paid by the patient, if any, as the copay edit.

If a patient does not receive a payment e-receipt, the patient knows their claim has not been submitted for adjudication and can address this issue immediately at the point of service to force claim submission. Since a claim reversal is also a possibility, a payment reversal e-receipt (typically in real-time, but at a time determined by the healthcare claims processor) indicating a claim reversal is sent to the patient enabling the patient to request corrective action if the patient did not authorize the claim reversal. Claim reversals are a problem when the service or product is received, even when the correct payment due is requested and paid because problems noted in items 2 through 6, herein, are experienced when such claims are reversed.

The preceding functions are fully integrated within a healthcare claim processor's online claims adjudication process using the present invention and they eliminate the potential for experiencing each of the six problems noted previously.

Healthcare claims processors include any entity that performs the function of receiving and adjudicating (or pre-adjudicating) healthcare claims that have been submitted by health care providers for the products and services they provide; and among other edits, healthcare claims processors provide health care providers information about their patients' financial responsibility (herein referred to as "copays"), and if applicable, the financial responsibility of third parties such as health plans and programs.

An e-receipt is an electronic notification, via e-mail, text/SMS, voice/audio, fax, push notification via a mobile app, etc., that, under the present invention not only verifies claim submission and adjudication, but also indicates the adjudicated price to be paid for the service/product received and the amount to be paid, if any, from the patient's source of funding based upon the availability of funds from the patient's registered funding source and/or the healthcare plan, if any. The payment e-receipt message notification is typically a real-time process, but the healthcare claims processor determines the timing. There are three payment possibilities: 1) full payment, 2) partial payment, and 3) no payment. The payment e-receipt: 1) assures the patient that their claim has been submitted and adjudicated, 2) indicates the total amount that is to be paid, 3) indicates the amount, if any, being funded via their previously provided source of funding for such payments (represented to the health care provider as the "plan" pay edit), and 4) indicates the amount to be paid by the patient, if any, as the copay edit.

If a patient does not receive a payment e-receipt, the patient knows their claim has not been submitted for adjudication and can address this issue immediately at the point of service to force claim submission. Since a claim reversal is also a possibility, a payment reversal e-receipt (typically in real-time, but at a time determined by the healthcare claims processor) indicating a claim reversal is sent to the patient enabling the patient to request claim resubmission if the patient did not authorize the claim reversal. An e-receipt is an electronic notification sent to the patient identifying the amount of a financial transaction that will be processed on behalf of the patient whose claim is being paid or reversed via the patient's provided personal funding source for such transactions. It typically includes additional claim related information.

Via the healthcare claim processor's integration of the real-time payment authorization request of the present invention for patient funds for healthcare provider ("plan") payment and both the patient payment and payment reversal e-receipt notifications (typically in real-time, but at a time determined by the healthcare claims processor) of the results thereof in their claims adjudication process, the present invention provides patients in an out-patient setting an ability at the point of service to: 1) force claim submission when providers fail to do it, 2) limit payment for their healthcare services and products to that as determined by the claims adjudication process rather than the provider's preference and 3) require providers to re-submit any claim reversal that does not have patient approval, approval that is typically limited to clinical issues or a price that exceeds a patient's ability or willingness to pay.

The present invention precludes claim adjudication circumvention via real-time healthcare claims processor-initiated payments to health care providers during the adjudication process on behalf of patients for their products and services when the patient's previously provided source of funding for their payments is adequate for such payment. The automated payment process initiated by the healthcare claims processor during the adjudication process and the corresponding patient payment e-receipt message notification (typically in real-time, but at a time determined by the healthcare claims processor) assures patients that they will always pay the correct, adjudicated amount to the health care provider. After a claim is submitted on-line for adjudication, the patient pricing/payment e-receipt notification is received at about the same time health care providers receive their pricing edits from the healthcare claims processor. Patients are then able to verify that their claims have been adjudicated and their payment is always for the correct amount. Additionally, the same e-receipt notification process (typically in real-time, but at a time determined by the healthcare claims processor) also enables patients to audit the health care provider's claim reversal actions, if any. Patients receive e-receipt message notifications: 1) after a response has been received from the patient's funding source regarding funds availability during the claims adjudication process, and 2) when claims have been reversed. Therefore, the absence of a payment e-receipt notification (typically in real-time, but at a time determined by the healthcare claims processor) indicates a claim has not been adjudicated and this enables patients to force health care providers to submit the claim for adjudication and charge them the correct discounted, contract rates as specified by the healthcare claims processor's pricing edits. Likewise, should the patient receive an payment reversal e-receipt notification that the health care provider has reversed a previously submitted and adjudicated claim, the patient, equipped with this knowledge, is now able to address the issue; and if the claim was unilaterally reversed by the health care provider, force the health care provider to re-submit the claim for adjudication so that the problems identified in items 2-6, herein can be eliminated.

The automated patient payment and e-receipt notification processes of the present invention that have been fully integrated within the healthcare claims processor's claims adjudication process provides a shift in control of the claims adjudication process from health care providers to patients and their healthcare claims processors by forcing health care providers to submit every claim for adjudication in all 100% copay situations. Health care providers' ability to unilaterally avoid claim submission or reverse claims is eliminated, as is each of the claims six problems that can be experienced when claims are not adjudicated. It also assures that claim reversals are limited to patient decisions such as the network discount price exceeding the patient's ability or desire to pay, clinical problems, etc., just as they are under traditional, fully funded health plans that employ a claim cost-sharing arrangement between the patient and health plan. The present invention provides pricing audit capability even in the case of insufficient (no) funds or credit from the patient's registered funding source and serves as a real-time payment solution that prevents claim adjudication circumvention by health care providers, placing the healthcare claims processor and patients, rather than the health care providers, in control. The present invention not only preempts the health care provider's ability to unilaterally circumvent the adjudication process, it also significantly diminishes the potential for health care providers to reverse claims because when the patient has sufficient funds availability from the patient's funding source, the pricing edits providers receive from the claims process indicate that the health plan will be paying for all or a part of the cost of the provider's product or service as is customary under fully funded plans.

When patients are registered to permit payments on their behalf from their provided source of funds and to receive e-receipt notifications via their preferred method, the present invention provides a patient claims processing payment solution via a real-time payment/e-receipt notification process that is fully integrated into the claims adjudication process which is applicable for all types of out-patient healthcare related claims, including, but not limited to: medical, prescription/pharmacy, dental, vision, durable medical equipment, laboratory, etc.) The present invention provides, in real-time and based upon patient funds availability, either a unique, patient (consumer) payment authorization or an audit of the health care providers' charges or claim reversals via the patient payment and payment reversal e-receipt message notifications which are received at about the same time health care providers receive their payment/reversal response pricing edits from healthcare claims processors in an out-patient setting. The present invention thereby eliminates providers' ability to treat patients as "cash cows" by: 1) circumventing the claims adjudication processes entirely, or 2) reversing claims without the patient's knowledge and charging "what the market will bear" rather than the discounted, adjudicated price providers have previously agreed to accept for their products and services. The present invention forces health care providers to submit claims and charge the appropriate discounted price without reversing claims absent the patient's knowledge or consent when patients are financially responsible for the entire charge (100% copay).

Also, under cash discount programs, healthcare claims processors typically charge health care providers for "patient steerage" and/or claim processing provided under their cash discount programs and forces provider compliance with contractual agreements. As previously noted, major pharmacy benefit management firms experience reversal rates ranging from twenty percent (20%) to fifty percent (50%) under their cash discount card programs, with those reversal rates ranging from four (4) to ten (10) times that experienced under traditional, fully funded, pharmacy benefit plans when patients' (cost-sharing) copays are approximately the same amount as the average prescription cost under the cash discount programs. Consequently, the increase in the reversal rate is not the result of consumer price considerations. By employing the present invention, pharmacy benefit management firms can expect to increase their cash discount card programs, High Deductible Health Plans (HDHPs) and Consumer Driven Health Plans (CDHPs) revenue.

At the healthcare claims processor's option, the present invention employs unique identifiers that enable patients in pharmacy cash discount programs to receive all of the advantages of cost-sharing programs, such as concurrent drug utilization review (DUR) to preclude such problems as duplicate therapy, drug incompatibilities, etc. Currently, for ease of enrollment under most, if not all, pharmacy cash discount programs, patients are enrolled without receiving a unique individual patient identifier; and the lack of individual patient identifiers precludes the provision of patient specific, concurrent DUR. Comparable advantages may also be available under other health care cash discount card programs.

Accordingly, the present invention provides a computerized method for payment of a product or service provided by a health care provider to a patient with full financial responsibility (100% copay) for real-time prevention of healthcare claim adjudication circumvention, comprising the steps of receiving a claim transaction for the patient who has previously provided a preferred method of electronic notification and a funding source; repricing the claim transaction to determine the financial responsibility for the respective parties (patient and health plan) for the healthcare product or service, the repricing including pricing edits indicating patient copay amount and "plan" pay amount; automatically initiating a real-time payment authorization request through a payment gateway for the patient portion of the adjudicated price; receiving a real-time notification through the payment gateway that the funding source has verified funds availability, if any, for the patient's financial responsibility; sending in real-time to the healthcare provider the copay and the "plan" pay pricing edits based on the adjudication of the claim and the patient funds availability, with the copay edit being defined as the then defined share of patient payment directly to the provider and the "plan" pay edit being defined as the amount debited from the patient's previously registered funding source; receiving a transfer of funds from the patient's funding source (credit transaction); and paying the health care provider the amount debited from the patient's funding source.

The present invention also provides a computerized method for payment of a product or service provided by a health care provider to a patient with full financial responsibility (100% copay) and e-receipt notification for real-time prevention of healthcare claim adjudication circumvention, comprising the steps of receiving a payment authorization request from a healthcare claims processor for a patient's financial responsibility for the product or service, based on the adjudication price of a claim transaction submitted by the healthcare provider, the payment authorization request including a unique patient identifier and a unique payment token associated with the patient's registered funding source(s); matching the unique patient identifier to the registered patient and the unique payment token to the patient's registered funding source(s); routing in real-time the payment authorization request to the patient's registered funding source; receiving in a real-time notification that the funding source has verified funds availability for the patient's financial responsibility ("plan" pay amount); notifying in real-time the healthcare claims processor of funds availability from the patient's funding source for the "plan" pay amount; sending in real-time to the healthcare provider the copay and the "plan" pay edits based on the adjudication of the claim, with copay being defined as the then defined share of patient payment directly to the provider and "plan" pay being defined as the amount debited from the patient's registered funding source, which precludes adjudication circumvention; electronically sending an electronic notification (e-receipt) in real-time indicating the patient's total financial responsibility and the amount of funds debited from their registered funding source, with the difference, if any, to be paid by the patient directly to the health care provider, whereby failure for the patient to receive an e-receipt indicates that the health care provider has failed to submit the claim for adjudication, thereby enabling the patient to request claim submission; and transferring the patient funds from the patients funding source to a designated account (credit transaction) to provide for health care providers' payments.

The present invention further provides a computerized method for payment of a product or service provided by a health care provider to a patient with full financial responsibility (100% copay) for real-time prevention of healthcare claim adjudication circumvention, comprising the steps of receiving a claim reversal from the health care provider for a previously submitted claim transaction for the patient who has provided a registered funding source; initiating in real-time a claim reversal payment authorization through a payment gateway; receiving in real-time notification that the funding source has confirmed receipt of the claim reversal payment authorization; and sending in real-time to the healthcare provider confirmation of a claim reversal confirmation edit.

The present invention further provides a computerized method for payment of a product or service provided by a health care provider to a patient with full financial responsibility (100% copay) and e-receipt notification for real-time prevention of healthcare claim adjudication circumvention, comprising the steps of receiving a claim reversal payment authorization request from a healthcare claims processor for a patient's previously submitted claim transaction and the corresponding payment authorization request, with the claim reversal payment authorization request including a unique patient identifier and a unique payment token associated with the patient's funding source(s); matching the unique patient identifier to the patient and the unique payment token to the patient's funding source(s); routing in real-time the claim reversal payment authorization request to the patient's registered funding source(s); receiving in real-time notification that the patient's funding source has confirmed receipt of the claim reversal payment authorization request; notifying the healthcare claims processor that the patient's funding source has confirmed receipt of the claim reversal payment authorization request; and electronically sending to the patient via the patient's preferred method of electronic notification a claim reversal payment e-receipt in real-time, indicating the patient's initial debit transaction has been credited back to the patient's account at the patient's funding source, thereby enabling the patient to request claim resubmission if the patient disagrees with the claim reversal.

The present invention further provides a computerized system for payment of a product or service provided by a health care provider to a patient with full financial responsibility (100% copay) and e-receipt notification for real-time prevention of healthcare claim adjudication circumvention, comprising healthcare provider computer for transmitting to a healthcare claims processor platform for claim adjudication of a claim transaction resulting from the patient's receiving a service or product from the healthcare provider, the health care provider computer for receiving the pricing edits from the healthcare claims processor platform of the claim transaction, the pricing edits including a copay amount and a "plan" payment amount for the patient's claim transaction; electronic notification server for sending, via the patient preferred method of electronic notification, a claim payment e-receipt to the patient at about the same time as the pricing edits are sent to the healthcare provider's computer, with the e-receipt indicating the patient's total financial responsibility and the amount of funds debited from their registered funding source, with the difference, if any, being the copay to be paid by the patient directly to the health care provider; and the failure for the patient to receive an e-receipt indicates that the health care provider has failed to submit the claim for adjudication, thereby enabling the patient to request claim submission; first application server for registration of personal information and a funding source of the patient for paying the patient's share of the claim cost and the patient's preferred method of receiving electronic notifications, the application server for assigning a unique patient identifier and a unique payment token, a second application server of the healthcare claims processor for sending member eligibility information to the first application server containing the patient's unique patient identifier and unique payment token, the first application server matching individuals identified in the member eligibility information with the corresponding patient's unique patient identifier and unique payment token, the first application server sending the patient identifiers and payment tokens to the second application server of the healthcare claims processor, the first application server for sending a payment authorization request from the healthcare claims processor adjudication platform to the patient's funding source through the payment gateway, with the patient funds to be deposited in a designated bank account for subsequent health care provider payment, the application server for sending the notification received from the funding source through the payment gateway to the healthcare claims processor, the first application server sending the patient (e-receipt) via the notification server to the patient; and the healthcare claims processor adjudication platform for receiving and adjudicating the claim transaction from the healthcare provider thus determining payment responsibilities, resulting from a healthcare provider providing a service or product to the patient, the healthcare claims processor platform for sending to the healthcare provider the copay amount and the "plan" pay amount (payment edits) based on the claim adjudication and patient funds availability at about the same time as the patient's receiving the e-receipt, whereby the patient is informed of the their financial responsibility owed to the healthcare provider in real-time to prevent the healthcare provider from circumventing the claim adjudication.

The present applicants have a co-pending patent application Ser. No. 15/474,566 ('566 application), herein incorporated by reference. The '566 application provides real-time patient pricing and claim reversal notifications, as an integrated component of the healthcare claims adjudication process, to enable patients to audit their health care provider charges and claim reversals, thereby eliminating the potential for healthcare claim adjudication circumvention. Under the present invention, patient payments to health care providers and corresponding patient e-receipt notifications are initiated by healthcare claims processors as an integrated component of the healthcare claims adjudication process to prevent claim adjudication circumvention.

DETAILED DESCRIPTION OF THE INVENTION

Figure 1:
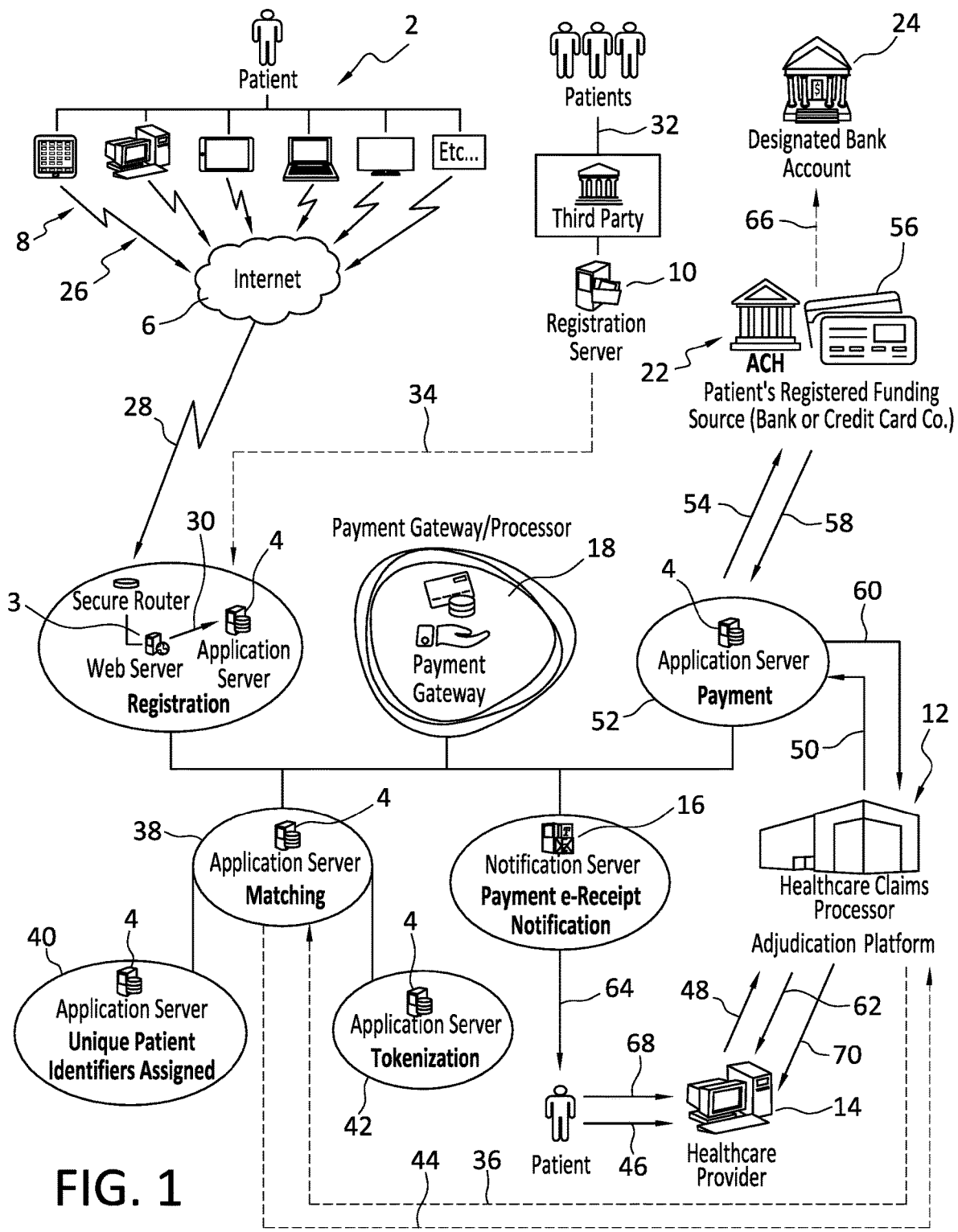
FIG. 1 is a schematic diagram of a system embodying the present invention showing a description of the process and responsibilities of the respective parties from patient registration to adjudication and payment for a submitted claim.

FIG. 1: Description of the Process and Responsibilities of the Respective Parties from Patient Registration to Adjudication and Payment for a Submitted Claim Referring to FIG. 1, a patient payment system 2 according to the present invention is disclosed. The system 2 includes a web server 3 operably connected to the internet 6. The web server 3 is operably connected to an application server 4 to receive a patient's registration information provided by the patient using a device 8, such a tablet, computer, smartphone, laptop, smart tv, operably connected to the Internet. A third party registration server 10 may also be used to transmit the patient's registration information to the application server 4.

The application server 4 is operably connected to a healthcare claims processor platform (hardware and software) 12, which is operably connected to a health care provider computer 14. The application server 4 is operably connected to a notification server 16. The application server 4 provides the functions of registration, matching, unique patient identifier assignment and payment e-receipt notification under the control of a payment gateway/processor 18. However, these functions may also be provided by the healthcare claims processor 12, a variety of entities such as MBR$_x$ or any third party. The healthcare claims processor includes an application server for sending member eligibility information to the application server 4 containing the patient's unique patient identifier and unique payment token. The application server 4 then sends the patient identifiers and payment tokens to the application server of the healthcare claims processor.

The server 4 also provides the functions of tokenization and payment under the payment gateway/processor 18. These functions are preferably performed only by the payment gateway/processor 18.

The present invention is fully integrated in the healthcare claims processor's claim adjudication platform 12. The patient's healthcare claim payment service, initiated by the healthcare claims processor 12, and the subsequent patient payment (and payment reversal, if any), e-receipt message notifications eliminate the health care provider's ability to unilaterally make a decision to circumvent the adjudication process and charge and collect an amount in excess of the adjudicated price when the patient is responsible for all charges (100% copay).

A provider's attempt to reverse a claim results in a patient claim payment reversal e-receipt message notification indicating the provider's action (FIG. 2); and unless requested or approved by the patient, the payment reversal e-receipt enables the patient to address the need for the provider to re-submit the claim unless they agree with the reversal. Basically, the patient payment system forces health care providers to submit claims and charge the correct, adjudicated price when patients are financially responsible for the entire charge (100% copay) for their health care products or services. The present invention also provides assurance that all of the previously noted six problems that can result from claim adjudication circumvention are eliminated.

The present invention can be employed to make patient co-payments under fully funded plans, which include a shared responsibility (both actual plan payments and actual patient co-payments) for the adjudicated amount due for the product or service, and for plans with patient co-payments after deductibles are met, but a reason for use would be to diminish potential patient confusion if the invention is used prior to deductibles being met and/or patient convenience. However, it would not be required to prevent claim adjudication circumvention due to the shared payment responsibility.

In addition to information which enables the matching of the registered individuals with their membership in the healthcare claims processor's member eligibility file, a patient registered for participation in the system provides a personal source of funding by registering their preferred method or instrument of payment (debit/credit card, bank draft account, ACH, or other then current payment method consistent with industry standards) to process a payment transaction for payments to health care providers on their behalf via the healthcare claims processor for the healthcare products and services they receive. In addition to providing their personal source of funding, the patient also provides their preferred method of notification (e-mail, text/SMS, voice/audio, fax, push notification via a mobile app, etc.) in order to receive payment and payment reversal e-receipt message notifications for claim payments and claim reversals. The preceding enables the patient to either know that their claim has been submitted and adjudicated, or force claim submission, thereby eliminating provider excess charges and the other five previously identified problems that can be expected when claims are not submitted for adjudication.

The healthcare claims processor's member eligibility file refers to the file that contains the list of plan members who have coverage under a health plan or program at any given time. When a claim is submitted by the health care provider, the healthcare claims processor receives the claim, and there is an attempt to electronically match the claimant with those members who are in the healthcare claims processor's member eligibility file to verify eligibility for coverage under the plan/program. If the claimant is listed in the healthcare claims processor's member eligibility file there is a match and the adjudication process continues. If the claimant is not in the member eligibility file, the claim is immediately rejected.

The healthcare claim processor's member eligibility file is used to match with those plan or program members that register for the patient payment system. When the information in the healthcare claims processor's member eligibility file matches the information provided by the individual registering for the patient payment system, the member is assigned both a unique identifier and a secure payment token which is sent to the plan/program and retained.

The registration, matching, unique patient identifiers assignment and payment e-receipt notification functions can be provided either exclusively by the payment gateway/ processor 18 or by a variety other entities that include the healthcare claims processor 12, or a third party performing one of more of the respective functions. Consequently, it should be noted that the present invention may be configured in several different ways to reflect the fact that one or more of those functions identified could be performed by various entities. The patient payment system shown in FIG. 1 assumes that the payment gateway/processor 18 performs each of these functions because of perceived advantages. However, if the healthcare claims processor 12 uses the process of the present invention, it would be making all related decisions. In any event, the party making the process configuration decisions could be expected to base decisions upon relevant concerns and the speed and cost of alternative process configurations because electronic claims processing is speed and cost sensitive.

The payment gateway 18 serves as "switch" for routing and processing payments and securely storing sensitive payment data. The payment processor is a financial institution that works in the background to provide all the payment processing services used by the healthcare claims processor 12 (merchant).

FIG. 1 depicts the process and responsibilities of the respective parties from the time of patient registration for the service provided by the present invention to that of the adjudication and payment for a submitted claim.

The patient (consumer/user/member) connects to the Internet to register in the system as depicted in Step 26, via a smartphone, desktop computer, tablet computer, laptop computer, a smart TV, etc. and navigates to the website hosted by a web server 3 in Step 28 to securely register the patient's personal information, which enables matching with the plan/program membership eligibility, including information required to employ the patient's preferred method of notification (e-mail, text/SMS, voice/audio, fax, push notification via a mobile app, etc.) and the patient's method or instrument of payment information (debit/credit card, bank draft account, ACH, or other then current payment method consistent with industry standards). The registered patient information is then transferred to the Application Server 4 as depicted in Step 30. The registered patient information can either be shared by MBRx, or a third party, with the healthcare claims processor 12 to serve as their enrollment in the healthcare claims processor's health plan and/or cash discount card program, or retained by MBRx, or a third party, for file matching purposes with the healthcare claims processor's then existing member eligibility file. Likewise, if the healthcare claims processor 12 secures the patient information, it can be retained and then shared with MBRx, or a third party, to serve as its registration information.

In addition to the patient registering in the system via the Internet 6, a third party (such as health plans/programs, various solution providers, etc.) may register multiple patients by securing the same information requested in Step 28 and sending that information to the application server 4 as depicted in Steps 32 and 34. Again, the registered patient information can either be shared by MBRx, or a third party, with the healthcare claims processor to serve as their enrollment in the healthcare claims processor's health plan and cash discount card program, or retained by MBRx, or a third party, for file matching purposes with the healthcare claims processor's then existing member eligibility file. Likewise, if the healthcare claims processor secures the patient information, it can be retained and then shared with MBRx, or a third party, to serve as its registration information.

In Step 36, the healthcare claims processor sends their member eligibility file information to the payment gateway/processor 18 and the patient's registration information that has been secured in Step 28 is matched in Step 38 with the healthcare claims processor's member eligibility file information. Furthermore, and not identified as a step, is the option of sharing the patient's registration information with the healthcare claims processor to serve as their enrollment eligibility in the healthcare claims processor's health plan or cash discount card program. Likewise, if the healthcare claims processor secures the patient information used for the registration, it can be retained and then shared with the payment gateway/processor to serve as its registration information for tokenization, etc. Each of the preceding precludes the need for the matching process in Step 38.

Step 40 represents the assignment of a unique patient identifier to each patient by the payment gateway/processor. When required, the assignment of the unique patient identifier can occur either before or after the matching process. Some healthcare claims processors may choose the assignment of the unique patient identifier to a family rather than to a patient.

Step 42 represents the assignment of a unique payment token for the preferred instrument or method of payment registered for each patient by the payment gateway/processor. The matching function can either precede or follow the secure tokenization process.

Tokenization defines a process through which a method or instrument of payment information is replaced with a surrogate identifier known as a "token". The security of an individual token relies on properties of uniqueness and the infeasibility to determine the original method or instrument of payment information knowing only the surrogate identifier. Where properly implemented, tokenization allows healthcare claims processors (merchants) to limit the storage of payment related information to within the tokenization system thereby, significantly reducing their risk exposure. As a reference or surrogate identifier for the original method or instrument of payment information, a token can be used by systems within the healthcare claims processor's environment without having to consider the security implications associated with the use of payment related data. Simply put, tokenization is a process that uses unique tokens in lieu of actual patient/member financial information such as bank routing and account numbers and payment card (debit/credit) numbers.

The process of the present invention will require at least one "unique" patient identifier to be used when everyone in the healthcare plan or program participates in the system and there is no potential for duplication of health plan or program patient identifiers. The process of the present invention will require the use of at least two "unique" patient identifiers when some members, but not others, in a healthcare plan or program participates in the system. Two "unique" patient identifiers also will be needed if there is any potential for duplication of any plan or program member IDs. Also, at the healthcare claims processor's option under some programs, the enrollee in the healthcare program and registered for the system may be assigned only one unique identifier that applies to all family members.

Although not required, but in order to reduce the healthcare claims processor's risk associated with having access to payment information and to avoid extensive payment card industry (PCI) regulation requirements, payment tokens are used in lieu of the patient's actual account (credit/debit card or bank account) information. The tokenization process provides the healthcare claims processor the secure storage of the patient's preferred method or instrument of payment information by linking a patient's unique identifier with a secure payment token that is used in lieu of the patient's actual credit or debit card information or bank account information.

As depicted in Step 44, the unique patient identifiers and unique payment tokens for matched patients are sent by the payment gateway/processor to the healthcare claims processor to be linked with the plan/program member identification number in the healthcare claims processor's member eligibility file and stored in a secure manner for use when a claim for a previously matched patient is being adjudicated. Likewise, if the patient's registration information is to be shared with the healthcare claims processor to serve as the patients' enrollment in their health plan or cash discount card program, the payment gateway/processor must assign the unique patient identifiers and unique payment tokens and provide the patient identifiers and tokens with the registered patient information to the healthcare claims processor as depicted in Step 44. Both the healthcare claims processor and the payment gateway/processor must possess the assigned unique patient identifiers and the assigned unique payment tokens for registered and matched patients in order to perform the payment and e-receipt functions.

In the event that the healthcare claims processor secures the patient's preferred method of payment and method of e-receipt notification information in the same file in which the health plan/program eligibility (enrollment) information is secured, a matching process is not required. However, unless the plan or program is limited to those participating in the system, a unique individual patient identifier is employed by the healthcare claims processor to identify only those registered for the system. Additionally, a payment gateway/processor assigned unique payment token for each patient's registered method of payment must be employed if the healthcare claims processor doesn't want access to, or knowledge of, patient related payment information. Otherwise, the healthcare claims processor would assume responsibility for the related risk and compliance with the payment card industry rules and regulations.

Step 46 depicts a patient registered for the system that is completely responsible for the full cost (100% copay), such as HDHPs, CDHPs, and cash discount card programs, when securing a product or service from a health care provider. The health care provider submits the claim of the patient to the healthcare claims processor for adjudication as depicted in Step 48. As depicted in Step 50, the amount of the patient's financial responsibility is determined by the healthcare claims processor, and the healthcare claims processor automatically initiates a real-time payment authorization request through the payment gateway/processor via API (or a then current file transfer method consistent with industry standards), with the required information that includes, among other information, the unique patient identifier, the unique payment token, and the patient's financial responsibility.

Step 52 represents the payment gateway/processor auto-matching the unique patient identifier and the unique payment token with the registered patient and the patient's preferred method or instrument of payment information in real-time.

Step 54 represents the payment gateway/processor forwarding, in real-time, the healthcare claims processor's payment authorization request to the patient's registered funding source via the payment processing network using the patient's preferred method or instrument of payment (debit/credit card, bank draft account, ACH, or other then current payment method consistent with industry standards) to satisfy the patient's financial responsibility.

Step 56 represents the patient's funding source processing the received payment authorization request.

Step 58 represents the patient's funding source real-time reply to the payment authorization request via the payment processing network and the payment gateway/processor indicating one of the following scenarios: 1) sufficient funding or credit is available to fully cover the entire payment requested ("full payment approved"); 2) funds availability to cover only a portion of the payment requested ("partial payment approved"); or 3) there are no funds or credit available to cover any of the payment requested ("declined payment").

Step 60 represents the payment gateway/processor's real-time payment authorization request reply to the healthcare claims processor's adjudication engine via API (or a current file transfer method consistent with industry standards) indicating the funds availability status. Upon receipt of the response to the real-time payment authorization request, the healthcare claims processor, in Step 62, sends real-time pricing and other edits to the health care provider indicating that the claim has been approved and the financial responsibilities of the respective parties ("plan" pay and patient copay pricing edits) for the adjudicated claim. The healthcare claims processors' adjudication platforms and health care providers' computer systems only identify two parties (the patient and a Third Party Payer, such as a health plan) for which the total reimbursement for the healthcare product or service is allocated. These two fields, patient pay amount (patient "copay") and Third Party Plan pay amount, will always equal the total adjudicated reimbursement due the health care provider. Based upon the real-time reply to the healthcare claims processor's payment authorization request using the registered patient's method of payment, as depicted in Steps 50-60, three (3) scenarios could result from the health care provider's perspective.

Scenario 1: Full Payment Approved—The payment authorization request is equal to the total adjudicated amount of the claim in 100% copay situations and if the amount is fully satisfied by the patient's preferred method of payment, the healthcare claims processor will send real-time pricing edits to the health care provider indicating the "plan" will pay the full amount of the claim and the amount to be collected directly from the patient (patient "copay") is $0.00 as depicted in both Steps 62 and 64. Subsequently, as indicated in Step 66 the patient's funds are moved from the patient's registered funding source to the healthcare claims processor's "Designated Bank Account" as indicated in the payment authorization request in order to provide the funds to pay the health care provider the entire adjudicated amount of the claim on behalf of the patient via the healthcare claims processor's or plan's normal method and payment cycle. Under this scenario, the share reported to the health care provider as "plan" pay actually will be paid to the health care provider by the healthcare claims processor via the process of the present invention facilitating full payment of the adjudicated price on behalf of the patient from the patient's registered funding source. This eliminates a health care provider's attempt to collect either the correct or an excessive payment directly from the patient.

In Step 64, the payment gateway/processor sends a payment e-receipt to the patient at approximately the same time as the pricing edits are sent to the health care provider thereby eliminating the health care provider's ability to collect any amount directly from the patient in Step 68.

In Step 70 the healthcare claims processor pays the health care provider the adjudicated amount of the "plan" payment for the claim as indicated in the plan payment edit provided in Step 62 pursuant to the healthcare claims processor's normal method and cycle of payment.

Scenario 2: Partial Payment Approved—If partial payments are permitted either when the payment authorization request exceeds the funding available from the patient's preferred method of payment because of limited funds or credit or there is a plan design that results in a payment authorization request which is less than the total adjudicated amount of the claim, the healthcare claims processor in Step 62 will send real-time pricing edits to the health care provider indicating the "plan" will pay a then defined share of the amount due to the health care provider. The defined "plan" share is the amount provided via the patient's funding source and the amount to be collected from the patient is the remaining balance due, the patient's copay as indicated in both Steps 62 and 64. In Step 68, the patient pays the patient's adjudicated copay, the appropriate amount of which is noted in Step 64 via the patient's payment e-receipt from the payment gateway/processor and is the share of the adjudicated amount that was not provided for "plan" payment from the patient's registered funding source via Step 66. Subsequently, as indicated in Step 66, the patient's funds for the adjudicated amount of the "plan" payment are moved from the patient's registered funding source to the healthcare claims processor's "Designated Bank Account" indicated in the payment authorization request in order to provide the funds to pay the health care provider on behalf of the patient via the healthcare claims processor's or plan's normal method and payment cycle in Step 70. Under this scenario, the health care provider perceives a cost-sharing arrangement as with fully funded plans, with the "plan" paying a share of the adjudicated price and the patient responsible for the direct payment of a share of the adjudicated amount (copay).

The preceding eliminates health care provider attempts to collect patient payments (copays) in excess of the adjudicated copay edits they receive, and the provision of the real-time payment e-receipts that are sent to patients in Step 64, eliminate any potential for excessive payments. plan design also could either preclude such partial "plan" payments under an "all or none" design or actually require partial payments via pre-defined patient copays with the balance due being "plan" payments via the payment authorization request process even if funds or credit for full "plan" payment is available.

Scenario 3: Declined Payment—If the amount in the payment authorization request is declined due to either no funds or credit available or by a plan design of an "all or none" payment and funds available are insufficient, the healthcare claims processor will send real-time pricing edits to the health care provider indicating the "plan" will pay $0.00 and the amount of the patient copay to be collected directly from the patient is the full adjudicated amount due to the health care provider as depicted in Steps 62 and 64 and the adjudicated amount of the health care provider's requested patient copay is confirmed by the provision of the patient payment e-receipt as indicated in Step 64.

Consequently, in Step 68, the patient pays the provider the total adjudicated price of the product or service received. There is no settlement of funds under Step 66 and no healthcare claims processor payment to the health care provider under Step 70. Although the "plan" payment edit reported to the health care provider indicates the "plan" pay is $0.00, and the patient copay edit indicates the patient is responsible for the full payment directly to the health care provider, the provision of the real-time payment e-receipt to the patient (Step 64) eliminates the health care provider's ability to collect more than the adjudicated price directly from the patient because it identifies the total adjudicated price for the product or service provided, thereby enabling the patient to audit the amount assessed by the health care provider].

In Scenarios 1 and 2 under FIG. 1, the healthcare claims processor's pricing edits represent to the health care provider that either the plan will pay the full cost, or there is a plan/patient cost-sharing arrangement which effectively eliminates the potential for the health care provider to unilaterally reverse the claim because of the "plan" paying either the total adjudicated amount or a share of the total adjudicated cost of the health care provider's product or service. Conversely, as depicted in Scenario 3 of FIG. 1, the healthcare claims processor's pricing edits indicate to the health care provider that the patient is completely responsible for the entire cost of the product or service being provided, thereby alerting the health care provider of the perceived ability to reverse the previously adjudicated claim and charge the patient a price that reflects the health care provider's preferred margins without detection from either the patient or the healthcare claims processor. However, the patient payment e-receipt that is provided in Step 64 eliminates that possibility via a patient audit.

At approximately the same time, or at a time designated by the healthcare claims processor, that the healthcare claims processor is sending the pricing edits to the health care provider in Step 62, the payment gateway/processor is sending a patient payment e-receipt notification to the patient in Step 64 via the patient's preferred notification method (e-mail, text/SMS, voice/audio, fax, push notification via a mobile app, etc.) indicating the claim has been adjudicated, the adjudicated price for the product or service, the amount of the "plan" payment transaction paid on the patient's behalf from the patient's funding source, if any, and the amount the patient owes directly to the health care provider, if any. The absence of a payment e-receipt message notification serves as a patient alert that the claim for which the health care provider is seeking payment directly from the patient has not been submitted and adjudicated and enables the patient to demand submission of their claim. Step 68 represents the direct patient payment of the patient's adjudicated "copay", if any, which is the amount that was not paid via the patient's registered funding source ("plan" payment), and was the amount communicated to the health care provider in Step 64. Step 66 depicts the settlement process in which the payment processing network settles the requested funds, if any, into the "designated bank account" as indicated in the payment authorization request in order for the healthcare claims processor to pay the health care provider for the product or service received on behalf of the patient via the healthcare claims processor's or plan's normal method and payment cycle in Step 70.

As indicated in Scenario 1, when patients have sufficient funds or credit available from their registered funding source and the design is for full payment by the "plan", the health care provider is paid on the patient's behalf by the "plan" using the funds processed from the patient's preferred method or instrument of payment. Therefore, the patient should not pay the health care provider directly because payment will be distributed to the provider according to the healthcare claims processor's or health plan's normal method and payment cycle. Even in the event of the patient having partial funds availability (as indicated in Scenario 2) or no funds available (as indicated in Scenario 3), the patient knows, with certainty, via the payment e-receipt notification (Step 64), that each claim was adjudicated, the adjudicated price of the product or service that is due to the health care provider, the amount that is to be paid to the health care provider directly by the patient (patient "copay"), if any, and the amount to be paid by the healthcare claims processor on behalf of the patient ("plan" payment), if any.

The preceding and claim reversal e-receipts (FIG. 2) eliminate the ability of a health care provider to circumvent the adjudication process without the patient's knowledge and ability to require claim submission, thereby placing the patient rather than the health care provider in control of the claim adjudication decision.

Figure 2:
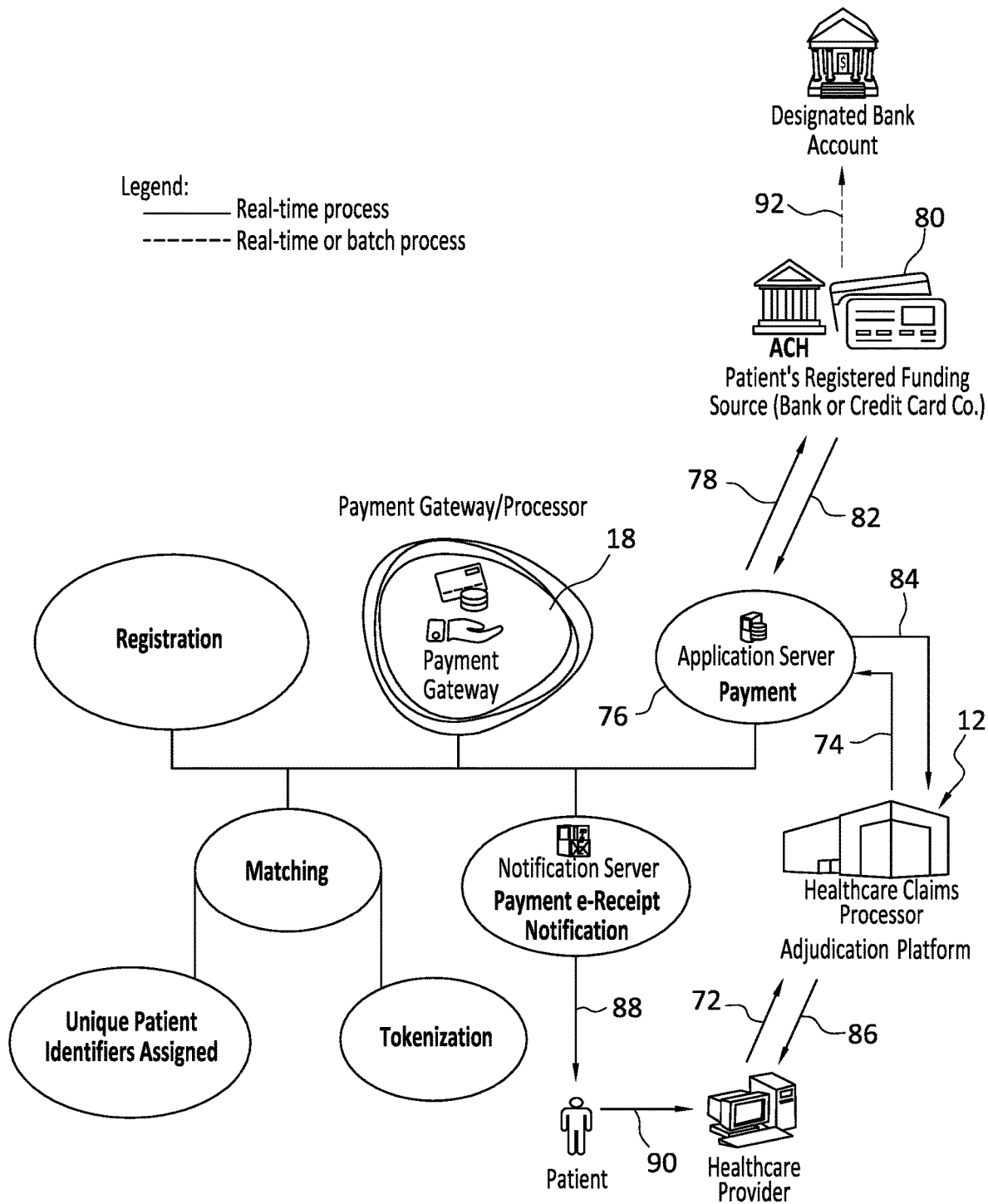
FIG. 2 is a schematic flow diagram of the process and responsibilities of the respective parties from the health care provider's submission of a claim reversal to the credit of funds to the patient's account.

Under the present invention, when the health care provider requests direct payment by the patient in Scenario 1, the patient knows with certainty that either: 1) the health care provider did not submit the claim (as evidenced by not receiving a payment e-receipt); 2) there is either only partial or insufficient funds available in their bank account (debit card/ACH), or their credit card credit limit was exceeded (as evidenced by receipt of the payment e-receipt); or 3) the health care provider submitted the claim and reversed it (as evidenced by receipt of the claim payment reversal e-receipt, as depicted in FIG. 2, below. E-receipts are typically sent to the patient in real-time; however, the healthcare claims processor determines the timing of its distribution.

Following patient registration, when one of their claims is submitted, the claim is adjudicated and this results in pricing edits being sent to the health care provider indicating either: 1) the "plan" will pay the full adjudicated amount; 2) a cost-sharing arrangement with the "plan" paying a share of the adjudicated price, and the patient responsible for direct payment of a share of the adjudicated amount; or 3) the patient is responsible for direct payment of the full adjudicated amount. Also, at approximately the same time the pricing edits are sent to the health care provider in Step 62, a payment e-receipt is sent to the patient in Step 64 indicating the claim has been adjudicated; the adjudicated price for the product or service; the amount of the "plan" payment transaction paid on the patient's behalf, if any; and the amount the patient owes directly to the health care provider, if any.

FIG. 2: Patient Payment System—A Description of the Process and Responsibilities of the Respective Parties from the Health Care Provider's Submission of a Claim Reversal to the Credit of Funds to the Patient's Account As depicted in FIG. 2, any and all attempts by a health care provider to circumvent the adjudication process by reversing a previously adjudicated claim without the patient's knowledge and consent is eliminated via the claim payment reversal e-receipt message notification that is sent to and received by the patient at approximately the same time as the health care provider receives the healthcare claims processor's edit documenting the claim reversal. Although typically in real-time, the timing of the claim payment reversal e-receipt is determined by the healthcare claims processor.

As in FIG. 1, the functions of registration, matching, unique patient identifiers assignment and payment e-receipt notification can be provided either exclusively by the payment gateway/processor 12 or by a variety other entities that include the healthcare claims processor, or a Third Party performing one of more of the respective functions. Consequently, it should be noted that FIG. 1 and FIG. 2 may be configured in several different ways to reflect the fact that one or more of those functions identified could be performed by various entities. However, because of perceived advantages, both FIG. 1 and FIG. 2 assume that the payment gateway/processor performs each of these functions. The party making the configuration decision could be expected to base decisions upon relevant concerns and the speed and cost of alternative configuration processes because electronic claims processing is speed and cost sensitive.

The process and responsibilities of the respective parties from the health care provider's submission of a claim reversal that results in the credit of funds to the patient's account, is depicted in FIG. 2.

Step 72 represents the health care provider electing to reverse a previously adjudicated claim by submitting a claim reversal request to the healthcare claims processor. Upon receipt of the claim reversal request, the healthcare claims processor, in Step 74, automatically initiates a claim payment reversal via a real-time payment authorization request (refund or void) through the payment gateway/processor via API (or then current file transfer method consistent with industry standards), with the required information that includes, among other information, the unique patient identifier, the unique payment token, and the claim's previously adjudicated "plan" payment of funds to be credited back to the patient's account from which it came.

Step 76 represents the payment gateway/processor auto-matching the unique patient identifier and the unique payment token with the registered patient and the patient's preferred method or instrument of payment information in real-time.

Step 78 represents the payment gateway/processor forwarding, in real-time, the healthcare claims processor's payment authorization request to the patient's registered funding source via the payment processing network using the patient's preferred method or instrument of payment (debit/credit card, bank draft account, ACH, or other then current payment method consistent with industry standards) to successfully credit the funds to the patient's account.

Step 80 represents the patient's funding source processing the received payment authorization request (refund or void payment).

Step 82 represents the payment processing network real-time response to the payment authorization request via the payment gateway/processor indicating funds will be credited back to the patient's account.

Step 84 represents the payment gateway/processor's payment authorization request real-time reply to the healthcare claims processor via API (or a current file transfer method consistent with industry standards) indicating funds will be credited back to the patient's account. Upon receipt of the real-time payment authorization, Step 86 represents the healthcare claims processor sending a real-time edit to the health care provider indicating the previously adjudicated claim has been reversed/voided.

Step 88 represents the payment gateway/processor sending a claim payment reversal e-receipt message notification (typically in real-time, but at a time determined by the healthcare claims processor) to the patient according to the patient's preferred notification method (e-mail, text/SMS, voice/audio, fax, push notification via a mobile app, etc.) indicating the claim has been reversed and the related financial transaction amount, if any, of the previous financial transaction has been reversed.

Step 90 represents the patient requesting that the health care provider re-submit the claim if the patient did not previously approve the claim reversal.

Step 92 represents the patient's funds that were originally debited to pay the health care provider on behalf of the patient, as depicted in FIG. 1, for the claim being reversed being credited to the patient's registered funding source (bank via debit card or ACH, credit card, etc.) as either a refund or void transaction.

Figure 3:
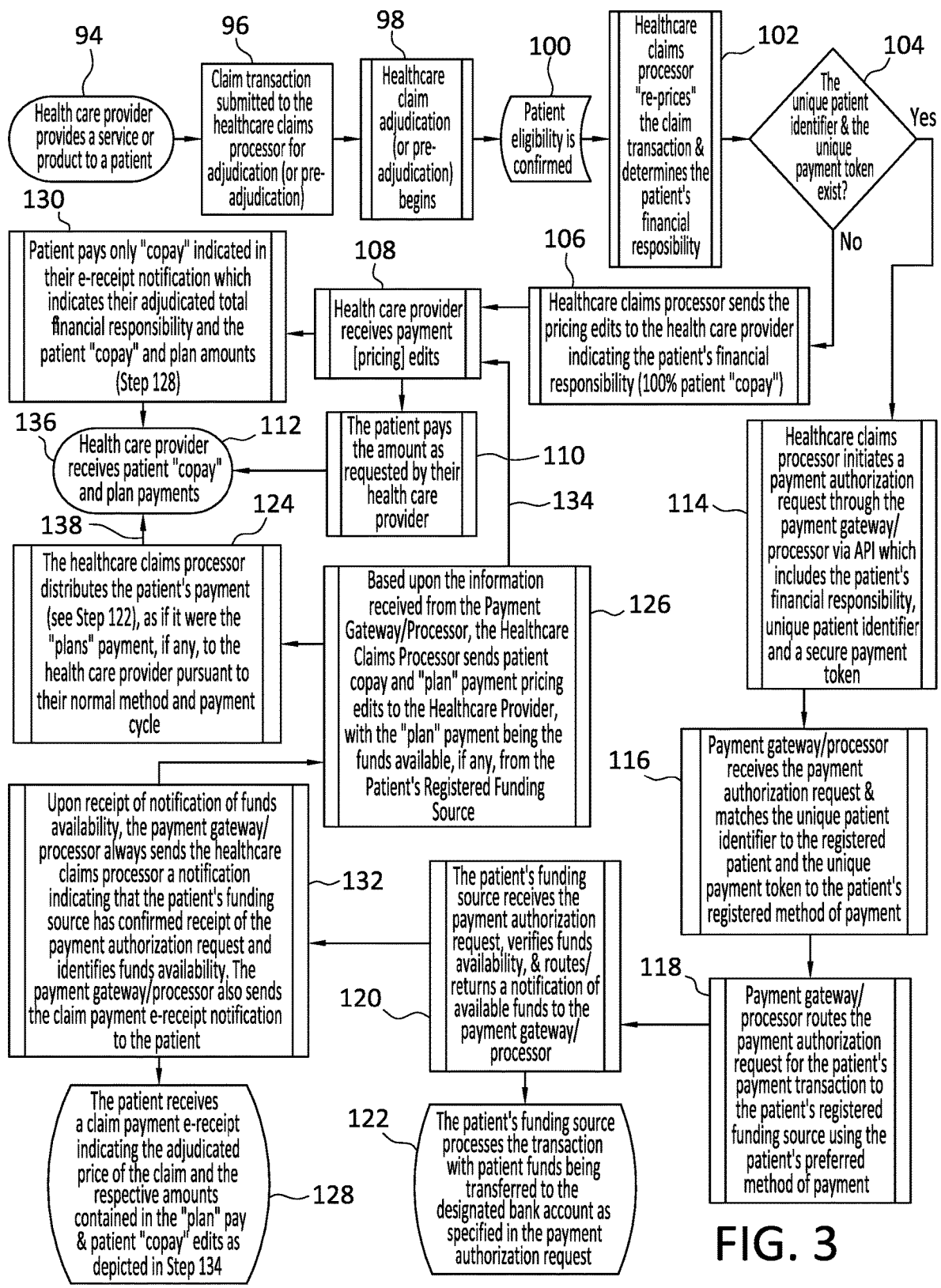
FIG. 3 is a flow diagram of the process embodying the present invention, showing a description of the responsibilities of the respective parties during and following the adjudication of a submitted claim.

FIG. 3: The Patient Payment Process—A Description of the Responsibilities of the Respective Parties During and Following the Adjudication of a Submitted Claim It should be noted that FIGS. 1 and 2 could have been configured in several different ways to reflect the fact that one or more of the functions of registration, matching, unique patient identifiers assignment and payment e-receipt notification could be performed by various entities. However, because of perceived advantages, the payment gateway/processor preferably performs each of them and this is reflected in both FIGS. 1 and 2. Consequently, in FIG. 3, the description assumes the payment gateway/processor performs each of these functions. The party making the configuration decision could be expected to base their decisions upon relevant concerns and the speed and cost of the alternative process configurations because electronic claims processing is speed and cost sensitive.

In order for healthcare claims processors to avoid the risk associated with having access to payment information, and to avoid extensive payment card industry regulation requirements, the system of the present invention uses payment tokens in lieu of the patient's actual credit or debit card information or bank account information. Through secure tokenization, the present invention provides secure storage of the patient's preferred method or instrument of payment information and eliminates the need for the healthcare claims processor to store and use the patient's actual credit or debit card or bank account information. However, without tokenization, the healthcare claims processor and the payment gateway/processor would each have to maintain a database that identifies the patient's preferred method or instrument of payment information for matching purposes.

Although tokenization is not required, there is the assumption that tokenization is employed. Consequently, when required or preferred, the payment gateway/processor will 1) develop and assign a unique patient identifier for each registered patient that is matched with someone in the healthcare claims processor's member eligibility file and a unique payment token is developed and assigned for each method or instrument of payment registered by the patient 2) send the unique patient ID and secure payment token to the healthcare claims processor to link with the healthcare claims processor's member ID in the healthcare claims processor's member eligibility file to satisfy the matching required when the payment gateway/processor receives a healthcare claims processor's payment authorization request after a member's claim has been submitted to the healthcare claims processor by a health care provider.

Step 94 represents a health care provider providing either a product or service to a patient registered for the claim payment service of the present invention; and Step 96 represents the health care provider submitting a claim to the healthcare claims processor for either pre-adjudication or adjudication.

Steps 98-102 represent the healthcare claims processor receiving the claim from the health care provider and implementing a process that the healthcare claims processor may utilize to adjudicate (or pre-adjudicate) an eligible claim which includes determining the financial obligations, if any, of the patient and the Third Party (health plan), the cumulative amount of which equals the total adjudicated amount owed to the health care provider. However, note that the sequence and functions may vary from healthcare claims processor to healthcare claims processor and the depicted process is not intended to be a comprehensive description of the typical healthcare claims processor's claim adjudication edits and process.

Step 104 identifies the decision point at which the healthcare claims processor determines if the claim is for a member registered for the service of the present invention; and if it is, it automatically begins the real-time process incorporated in the healthcare claims processor's claim adjudication process in all 100% copay situations. The healthcare claims processor determines if the patient whose claim is being adjudicated has a unique patient identifier associated with that patient and a unique payment token associated with the patient's registered method or instrument of payment. If a unique patient identifier and an associated unique payment token do not exist, the healthcare claims processor proceeds to Step 106 in which the healthcare claims processor sends edits to the health care provider indicating the patient copay is the entire adjudicated cost of the product or service received and the plan payment is $0.00. The edits are received by the health care provider in Step 108 and in Step 110, the patient pays the health care provider's quoted cost for the product or service received, a quoted cost which may or may not be the same as the adjudicated cost. In Step 112 the health care provider receives the requested payment. Steps 106 through 112 depict the traditional process of sending the health care provider edits that include pricing edits that indicate the adjudicated amount of the patient copay and that of the plan payment under the member's plan or program.

As with all traditional 100% copay scenarios (claims before a patient reaches their deductible or under all cash discount card programs) these pricing edits that are sent to the health care provider currently indicate the provider should collect the entire adjudicated amount directly from the patient and the plan will pay nothing. If a unique patient identifier and an associated unique payment token exist, the healthcare claims processor automatically proceeds to Step 114; and as depicted in FIG. 3, Step 114 and the steps thereafter are steps in the healthcare claims processor's claim adjudication process to eliminate health care provider claim adjudication circumvention and the six problems that are otherwise experienced. Steps 114 through Step 138, below, represent the various steps in the process of the present invention.

In Step 114, the healthcare claims processor's adjudication engine automatically initiates a payment authorization request via API (or a then current file transfer method consistent with industry standards) through the payment gateway/processor.

In Step 116, the payment gateway/processor receives the payment authorization request from the healthcare claims processor, matches the unique patient identifier to the registered patient, and via their unique payment token, matches the patient's registered method of payment/funding source (debit/credit card, bank draft account, ACH, or other then current payment method consistent with industry standards).

In Step 118, the payment gateway/processor routes the payment authorization request to the funding source of the patient's preferred method or instrument of payment (debit/credit card, bank draft account, ACH or other then current payment method consistent with industry standards).

In Step 120, the patient's preferred funding source receives the payment authorization request for the funds to pay the health care provider the "plan" payment, verifies funds availability, and returns a notification of available funds, if any, to the payment gateway/processor. Because of the potential for patient confusion, there is reason to expect the healthcare claims processor to require an "all or none" response to a payment authorization request for the funds to pay the entire adjudicated cost of a claim even though funds might be available for partial but not full payment. The healthcare claims processor also has the option to provide for defined patient copay(s) and a variable "plan" payment via the payment authorization request. As indicated in Step 122, if credit or funds are available to completely satisfy the healthcare claims processor initiated payment authorization request (either full or partial payment), the patient's funding source processes the transaction with the funds being deposited in the healthcare claims processor's designated bank account as specified in the payment authorization request to satisfy the "plan" share of the adjudicated cost of the product or service received, with the "plan" payment to the health care provider thereafter being made by the healthcare claims processor pursuant to the healthcare claims processor's normal method and payment cycle. Likewise, if partial payments are permitted when the amount requested is unavailable, that available amount is deposited and becomes the "plan" share of the adjudicated cost. If partial payments are either not permitted, or there is no credit or funds available for any payment, there will be no deposit of funds in the healthcare claims processor's designated bank account (Step 122) and no "plan" payment as depicted in Step 124. Consequently, there are three possible patient funding source responses to the payment authorization request: full funding, partial funding, or no funding as indicated in the three Scenarios below.

Scenario 1: Full Claim Payment Approved—If the payment authorization request is equal to the total adjudicated amount of the claim and the amount can be fully satisfied by the patient's preferred method of payment, the healthcare claims processor will send real-time pricing edits to the health care provider indicating the "plan" will pay the full amount of the claim and the amount to be collected from the patient (patient "copay") is $0.00 as indicated in Step 126. Subsequently, as indicated in Step 122, the patient's funds are moved from the patient's registered funding source to the healthcare claims processor's "Designated Bank Account" as indicated in the payment authorization request in order to provide the funds to pay the health care provider the entire adjudicated amount of the claim on behalf of the patient via the healthcare claims processor's normal method and payment cycle in Step 124. Under this scenario, the share reported to the health care provider as "plan" pay actually will be paid to the health care provider via the process of the present invention facilitating full payment of the adjudicated amount of the claim on behalf of the patient which eliminates a health care provider's attempt to collect payment directly from the patient. In Step 128, the payment gateway/processor sends a claim payment e-receipt to the patient at approximately the same time as the pricing edits are sent to the health care provider in Step 126, thereby eliminating, via the patient's payment e-receipt in Step 128, the healthcare provider's ability to collect any amount directly from the patient in Steps 130/112.

Scenario 2: Partial Payment Approved—If partial payments are permitted either when the payment authorization request exceeds the funding available from the patient's preferred method of payment because of limited funds or credit or there is a plan design that results in a payment authorization request which is less than the total adjudicated amount of the claim, the healthcare claims processor in Step 126 will send real-time pricing edits to the health care provider indicating the "plan" will pay either the amount of available funds or a then defined share of the adjudicated amount due to the health care provider. The defined "plan" share is the amount provided via the patient's funding source and the amount to collect from the patient is the remaining balance due, the patient's copay. In Step 130, the patient pays the patient's adjudicated copay, the appropriate amount of which is provided to and received by the patient in Step 128 via the patient's claim payment e-receipt from the payment gateway/processor and is the share of the adjudicated amount that was not provided for "plan" payment in Step 124 via Step 120 from the patient's registered funding source. As indicated in Step 122, the patient's funds for the adjudicated amount of the "plan" payment are moved from the patient's registered funding source to the healthcare claims processor's "Designated Bank Account" indicated in the payment authorization request in order to provide the funds to pay the health care provider on behalf of the patient via the healthcare claims processor's normal method and payment cycle in Step 124. Under this scenario, the health care provider perceives a cost-sharing arrangement with the "plan" paying a share of the adjudicated price, and the patient responsible for the direct payment (copay) of a share of the adjudicated amount. This eliminates health care provider attempts to collect patient payments (copays) in excess of the adjudicated copay edits they receive in Step 126; and the provision and receipt of the real-time payment e-receipts that are sent to and received by patients in Step 128 eliminates any potential for excessive payments. Plan design also could either preclude such partial "plan" payments under an "all or none" design or actually require them via pre-defined patient copays with the balance due being "plan" payments via the payment authorization request process even if funds or credit for full "plan" payment is available.

Scenario 3: Declined Payment—If the requested amount in the payment authorization request is declined due to either no funds or credit available or by a plan design of an "all or none" payment when some but not all funds are available for payment, the healthcare claims processor will send real-time pricing edits to the health care provider in Step 126 indicating the "plan" will pay $0.00 and the amount of the patient copay to be collected directly from the patient in Step 130 is the full adjudicated amount due to the health care provider as indicated in both Steps 126 and 128. The validity of the adjudicated amount of the health care provider's requested patient copay is confirmed by the provision and receipt of the patient payment e-receipt in Step 128. Consequently, in Step 130, the patient pays the provider only the adjudicated price of the product or service received and there is no settlement of funds under Step 122 and no "plan" payment in Step 124. Although in Step 126 the "plan" payment edit reported to the health care provider as "plan" pay is $0.00, and the patient copay edit indicates the patient is responsible for the full payment directly to the health care provider, the provision of the patient's real-time payment e-receipt in Step 128 eliminates the health care provider's ability to collect more than the adjudicated price directly from the patient because it identifies the total adjudicated price to be paid.

In Scenarios 1 and 2 under FIG. 3, the healthcare claims processor's pricing edits in Step 126 represent to the health care provider that either the "plan" will pay the full cost, or there is a "plan"/patient cost-sharing arrangement which eliminates the potential for the health care provider to reverse the claim due to the "plan" paying either the total adjudicated amount or a share of the total adjudicated cost of the health care provider's product or service. Conversely, as depicted in Scenario 3 of FIG. 3, the healthcare claims processor's pricing edits in Step 126 indicate to the health care provider that the patient is completely responsible for the entire cost of the product or service being provided, thereby alerting the health care provider of the perceived ability to reverse the previously adjudicated claim and charge the patient a price that reflects the health care provider's preferred margins without detection from either the patient or the healthcare claims processor. However, the patient payment e-receipt that is provided and received in Step 128 eliminates that possibility.

Upon receipt of the funds availability message from the patient's registered funding source, the payment gateway/processor in Step 132 sends the healthcare claims processor, a message indicating the funds availability status from the patient's funding source for the health care provider's "plan" edit/payment. In Step 126, the healthcare claims processor receives the notice of funds availability from the payment gateway/processor and sends plan payment and patient copay pricing edits to the health care provider. At about the same time and as indicated in Step 128, the payment gateway/processors sends and the patient receives a payment e-receipt via the patient's preferred notification method (e-mail, text/SMS, voice/audio, fax, or push notification via a mobile app, etc.) typically in real-time, but at a time determined by the healthcare claims processor. The patient e-receipt verifies claim submission and adjudication, identifies the amount to be paid, if any, from the patient's registered funding source ("plan" payment), the amount, if any, to be paid directly by the patient (copay), and the total adjudicated amount due for the product or service the patient has received ("plan" pay plus patient copay). The healthcare claims processor may choose to send the e-receipt message notifications to patients.

Based upon the response to the payment authorization request from the payment gateway/processor the healthcare claims processor in Step 126 sends the health care provider "plan" and patient copay pricing edits, with the plan edit based upon the funds available information received in the response to the payment authorization request in Step 132. In Step 134, the health care provider receives the pricing edits from the healthcare claims processor. In Step 130, the patient pays the health care provider the claim adjudicated copay, if any, as indicated in the pricing edit from the healthcare claims processor in Step 126 and as confirmed in the patient payment e-receipt in Step 128. In Step 136 the health care provider receives the patient copay. In Step 124, the healthcare claims processor pays the healthcare provider the "plan" share of the adjudicated cost of the claim, if any, via its normal method and payment cycle; and in Step 138, the health care provider receives the adjudicated "plan" payment indicated in the pricing edit received from the healthcare claims processor in Step 14.

In Steps 114, through Step 138, the payment gateway/processor via a match with the unique patient identifier and payment token route a health care claims processor's payment authorization request for a transaction from the patient's preferred method or instrument of payment (debit/credit card, bank draft account, ACH, or other then current payment method consistent with industry standards) to the healthcare claims processor's designated bank account for the funds to satisfy the patient's adjudicated financial responsibility for the product or service received from the health care provider. Upon receipt of funds availability for a "plan" payment from the patient's registered funding source, the payment gateway/processor sends the healthcare claims processor the funds availability for "plan" payment and the patient a payment e-receipt using the patient's preferred notification method (e-mail, text/SMS, voice/audio, fax, or push notification via a mobile app, etc.) typically in real-time, but at a time determined by the healthcare claims processor, that verifies claim submission and adjudication, identifies the amount to be paid, if any, from the patient's registered funding source ("p" payment), the amount, if any, to be paid directly by the patient (patient copay), and the total adjudicated amount due for the product or service ("plan" pay plus patient "copay). If the healthcare claims processor uses the present invention, it may choose to send the e-receipt message notifications to patients. Following receipt of the amount of available funds for "plan" payment from the payment gateway/processor, the healthcare claims processor sends the health care provider both plan and patient pricing edits; the patient pays the health care provider the adjudicated patient Copay, if any; and the healthcare claims processor pays the health care provider the adjudicated "plan" payment, if any, via their normal method and payment cycle.

The claim payment service of the present invention that includes a patient payment e-receipt message notification verifies to the patient that the claim has been submitted and adjudicated and represents to the health care provider that the available funds from the patient's registered funding source, if any, as coming from the health plan. When funds available from the patient's funding source enable only partial payment approval and plan design permits it, the partial payment, if any, is reported as a "plan" payment and the balance due is reported as a patient copay responsibility. If there is a complete lack of funds or credit (declined payment) available from the patient's registered funding source, the healthcare provider receives edits that indicate the entire adjudicated cost of the product or service received is the patient's copay responsibility and there is no "plan" share responsibility.

Since the patient receives a payment e-receipt each time a claim is adjudicated, the present invention eliminates the health care provider's ability to unilaterally circumvent the adjudication process and charge and collect an amount in excess of the adjudicated price even when the patient is responsible for all charges (100% copay). When the patient fails to receive a payment e-receipt, they can demand claim submission, and when they receive the payment e-receipt, they not only know that their claim was submitted and adjudicated but also know if and how much is to be paid to the health care provider and by whom.

The present invention's patient claim payment service that includes a patient payment e-receipt message notification verifies to the patient that the claim has been submitted and adjudicated. The present invention's process represents to the health care provider via the healthcare claims processor's pricing edits that the available funds providing full or partial payment from the patient's registered funding source, if any, as coming from the plan. It also indicates to both the patient and health care provider the amount to be paid as a "plan" payment, if any, and the amount to be collected directly from the patient, if any, as a copay. The present invention eliminates the health care provider's ability to unilaterally circumvent the adjudication process and charge and collect an amount in excess of the adjudicated price when the patient is responsible for all charges (100% copay). The present invention eliminates the six problems that can be experienced when claim adjudication is circumvented.

The present invention requires at least one "unique" patient identifier to be used when everyone in the health care plan or program participates in the system and there is no potential for duplication of health plan or program patient identifiers. The present invention requires the use of at least two "unique" patient identifiers when some members, but not others, in a healthcare plan or program participates in the system. Two "unique" patient identifiers also will be needed if there is any potential for duplication of any plan or program member IDs. Also, at the healthcare claims processor's option under some programs, the enrollee in the healthcare program and registered for system of the present invention may be assigned only one unique identifier that applies to all family members.

Figure 4:
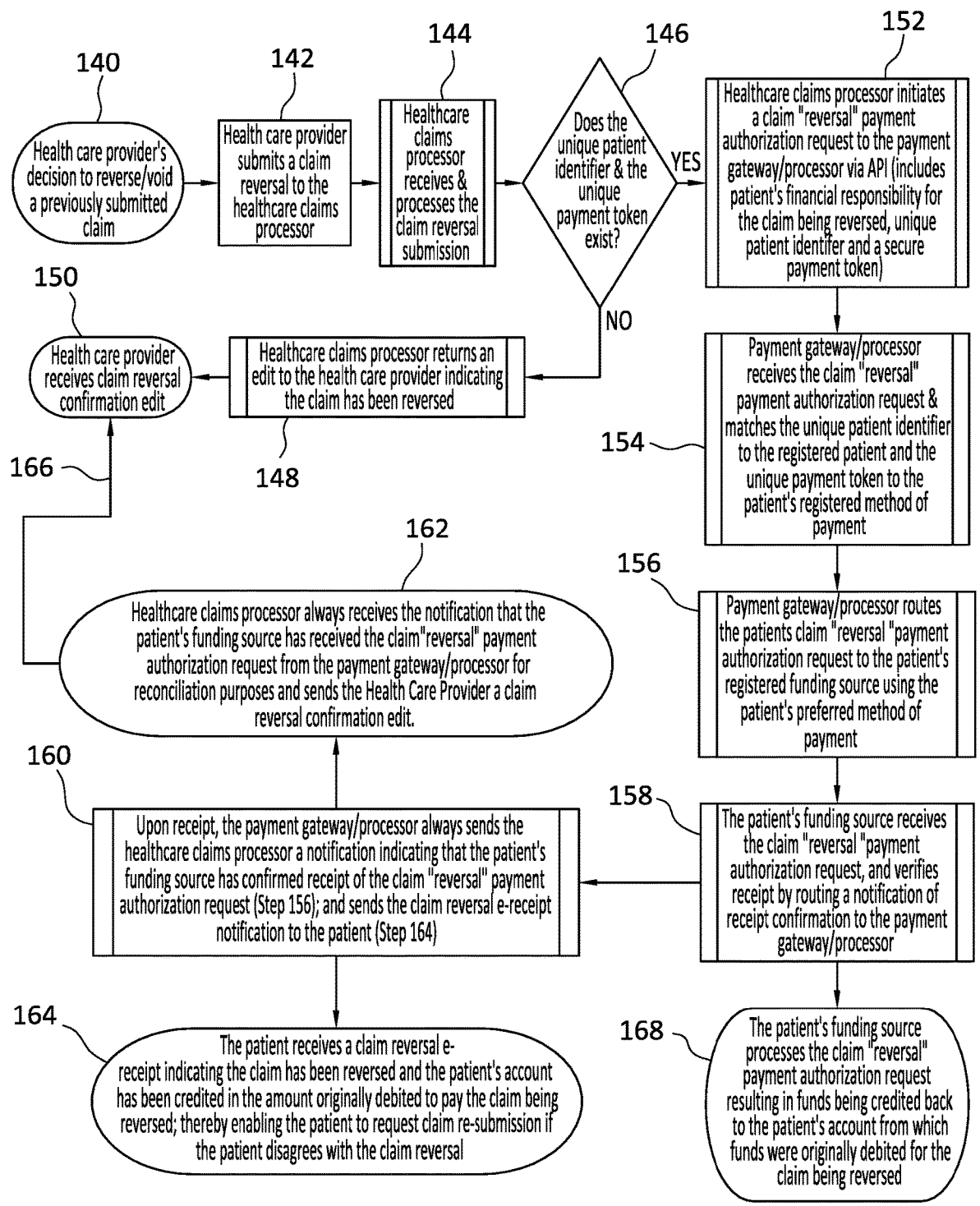
FIG. 4 is a flow diagram of the process embodying the present invention, showing a description of the responsibilities of the respective parties during and following the adjudication of a claim reversal.

FIG. 4: A Description of the Responsibilities of the Respective Parties During and Following the Adjudication of a Claim Reversal Step 140 represents a health care provider's decision to reverse or void a previously submitted and adjudicated claim for a registered patient; and Step 142 represents the health care provider submitting the claim reversal request to the healthcare claims processor. Step 144 represents the healthcare claims processor receiving a health care provider's claim reversal submission under its traditional process for reversing a previously submitted claim. Step 146 represents the beginning of claim reversal process of the present invention to be incorporated as a component of the health care claims processor's claim reversal process in which the healthcare claims processor determines if the patient whose claim is being reversed has a unique patient identifier associated with the registered patient and a unique payment token associated with the patient's registered method or instrument of payment. If the unique patient identifier and the unique payment token do not exist, the healthcare claims processor proceeds to Steps 148 and 150, which is the healthcare claims processor's traditional process of sending the health care provider an edit indicating the claim has been reversed or voided. If the unique patient identifier and the unique payment token do exist, the healthcare claims processor proceeds with the claim reversal process outlined in Steps 152 through Step 168.

Steps 152-168 represents a real-time process according to the present invention incorporated as a component of the health care claims processor's claim reversal process in which the healthcare claims processor initiates a claim reversal payment authorization request for the claim being reversed via API (or a then current file transfer method consistent with industry standards) to the payment gateway/processor to route a payment reversal transaction via the patient's preferred method or instrument of payment (debit/credit card, bank draft account, ACH, or other then current payment method consistent with industry standards) for processing in order to fully credit the patient's funding source for the amount of funds that were originally debited for the purpose of paying the health care provider on the patient's behalf for the claim being reversed. The payment gateway/processor via a match with the unique patient identifier and payment token routes the healthcare claims processor's payment reversal authorization request to the patient's funding source. The patient's funding source receives the reversal payment authorization request and acknowledges receipt thereof by routing a notification confirming receipt to the payment gateway/processor. Upon notification of the receipt of the reversal payment authorization request from the patient's funding source, the payment gateway/processor sends the healthcare claims processor notification that the patient's funding source has received the claim reversal payment authorization for processing and sends the patient a claim payment reversal e-receipt using the patient's preferred notification method (e-mail, text/SMS, voice/audio, fax, or push notification via a mobile app, etc.) typically in real-time, but at a time determined by the healthcare claims processor, verifying a claim reversal and indicating the funds originally debited have been refunded, or credited, back to the patient's registered funding source. Upon receipt of the reversal notification message from the payment gateway/processor the healthcare claims processor sends the health care provider a claim reversal confirmation edit.

The present invention eliminates the health care provider's ability to unilaterally make a decision to circumvent the adjudication process and charge and collect an amount in excess of the adjudicated price when the patient is responsible for all charges (100% copay) by reversing a previously submitted claim. A provider's attempt to reverse a previously submitted and adjudicated claim results in a patient claim payment reversal e-receipt message notification being sent to the patient (typically in real-time, but at a time determined by the healthcare claims processor) indicating the provider's reversal action and the restoration of funds previously debited from their funding source for the payment of the claim being reversed. This enables the patient to address the need for the provider to re-submit the claim unless the patient concurs in the decision.

Step 140 represents a health care provider's decision to reverse a previously submitted claim that was originally submitted for a registered patient; and Step 142 represents the health care provider submitting the claim reversal to the healthcare claims processor.

Step 144 represents the process of a healthcare claim processor receiving a health care provider's claim reversal submission and its traditional process for reversing or voiding a previously submitted claim.

Step 146 represents the beginning of the claim reversal process according to the present invention incorporated as a component of the health care claims processor's claim reversal process in which the healthcare claims processor determines if the patient whose claim is being reversed has a unique patient identifier and a unique payment token associated with the patient. If the unique patient identifier and the unique payment token do not exist, the healthcare claims processor proceeds to Steps 148 and 150, which is the traditional process of sending the health care provider an edit indicating the claim has been reversed. If the unique patient identifier and the unique payment token do exist, the healthcare claims processor proceeds with the claim reversal process outlined in Steps 152 through Step 168.

In Step 152, the healthcare claims processor automatically initiates a payment "reversal" payment authorization request to the payment gateway/processor via API (or a then current file transfer method consistent with industry standards) to process a payment transaction via the patient's preferred method or instrument of payment (debit/credit card, bank draft account, ACH, or other then current payment method consistent with industry standards) to fully credit the patient's funding source for the amount of funds that were originally debited for the purpose of paying the health care provider on the patient's behalf for the claim being reversed. In Step 154, the payment gateway/processor receives the claim reversal payment authorization request and via the unique patient identifier and unique token, matches it to the patient's method of payment for the payment reversal. In Step 156 the payment gateway/processor routes the claim reversal payment authorization request to the funding source for the patient's previous payment for the claim for which the reversal is being requested; and in Step 158 the patient's funding source receives the claim reversal payment authorization request and verifies receipt by routing a notification of the receipt of the claim reversal payment authorization request to the payment gateway/processor. In Step 160, the payment gateway/processor receives the notification that the patient's funding source has received the claim reversal payment authorization request and sends the healthcare claims processor a notification message that the patient's funding source has confirmed receipt of the claim reversal payment authorization request. In Step 162, the healthcare claims processor receives a confirmation notification that the patient's funding source has received the claim reversal payment authorization request, thereby satisfying reconciliation needs; and in Step 164, the payment gateway/processor sends the patient a claim payment reversal e-receipt via the patient's preferred notification method (e-mail, text/SMS, voice/audio, fax, or push notification via a mobile app, etc.) typically in real-time, but at a time determined by the healthcare claims processor. The claim payment reversal e-receipt enables the patient to request the re-submission of the claim unless the patient has requested or agrees with the decision to reverse the claim. If the healthcare claims processor may choose to send the patient e-receipts. In Step 166, the healthcare claims processor sends the health care provider a claim reversal confirmation edit. In Step 168, the patient's funding source processes the claim reversal payment authorization request (via payment reversal or void payment) which results in the amount of the requested funds being credited back to the patient's account at the patient's funding source from which the funds had been debited to pay for the claim being reversed.

Some healthcare entities may have tried to address the problem of health care providers circumventing the claim adjudication process under HDHPs, including CDHPs, prior to patients meeting their deductible for the purpose of securing a higher reimbursement than the health care provider's contracted reimbursement rate via a retrospective process. One retrospective process entails the provision of an Explanation of Benefits (EOBs) via an online portal to permit patients to access their claim(s) history and verify their claims have been adjudicated without being reversed and the amount paid was the contractually correct amount as indicated therein. Another retrospective process is the periodic provision of hardcopy EOBs that summarize the claims received and adjudicated. Unfortunately, neither of the preceding retrospective approaches enable health plans and healthcare claims processors to track or measure the occurrence of claim adjudication circumvention because of the relative rarity of patients taking advantage of the information available to them on a consistent basis. Therefore, any conclusions drawn from healthcare claims processors' related experience could be expected to be misleading and contribute to the significance of the problem as it relates to HDHPs and CDHPs. Until they do the comparative research related to this issue, they may not recognize the magnitude of the problem and its impact on patient expense and quality of care. Both of the preceding retrospective processes fail to prevent claim adjudication circumvention.

Conversely, the present applicants' conclusions were derived from an approach that involved researching Pharmacy Benefit Management firms (PBMs) claim reversal rates: 1) under cash discount card programs in which patients are always responsible for the payment of the full discounted fee (100% copay); and 2) under traditional cost sharing plans with defined, cost-sharing copays. The applicants' research discovered measurable indicators that provide insight into the frequency and magnitude of the claim adjudication circumvention problem. The research indicated that it is not uncommon for PBMs to experience reversal rates of 20 to 50 percent under their cash discount programs and all of the PBMs we researched indicated surprise that their reversal rates were so high, thereby indicating that they either had not made an effort to evaluate the need for a solution or had not been able to formulate one. The reversal rates were approximately four (4) to ten (10) times greater than reversal rates experienced under fully funded plans that have defined, cost-sharing copays (based on a 2010 CVS Caremark press release regarding research that found a correlation between the amount of the patient co-pay and the prescription abandonment rate) when the average prescription cost is approximately the same as the copayment identified in the CVS Caremark research. Therefore, the cost of prescriptions is not the reason for the difference in reversal rates. As a result of these statistics, it is logical to conclude that health care providers' ability to unilaterally make reversal decisions (without the PBM's consent or the patients' knowledge or consent) in all 100% copay situations plays an important role in the frequency of reversals and the resulting increases in consumers' out-of-pocket expenses, as well as the five other significant problems that can be experienced as noted herein.

As opposed to the previously described retrospective approaches, the present invention prevents health care providers from circumventing the adjudication process without their patients' knowledge, thereby negating the problems incurred under retrospective processes. The present invention provides a real-time healthcare claims processor initiated patient payment authorization request and a patient e-receipt message notification process (typically in real-time, but at a time determined by the healthcare claims processor). The present invention enables patients to have their payments made to the health care provider on their behalf; and based upon funds availability from the patient's funding source, patients 1) pay nothing directly to the health care provider; 2) only make a partial payment to the health care provider; or 3) pay the health care provider directly due to no funds or credit, with the e-receipt notification indicating 1) the total amount due for the service or product; 2) the authorized amount to be paid, if any, via the healthcare claims processor real-time initiated payment authorization request during the adjudication process utilizing the patient's provided funding source ("plan" payment), if any; and 3) the amount to be paid by the patient directly to the health care provider (patient "copay"), if any.

The process according to the present invention provides that patient claims are submitted and adjudicated, counted toward their deductibles, and the payments requested by health care providers, if any, are the correct amounts. The absence of a patient e-receipt message notification (typically in real-time, but at a time determined by the healthcare claims processor) indicates that their claims have not been submitted for adjudication; and this enables patients to address this issue by forcing health care providers to submit their claims for adjudication and charge them the adjudicated, discounted rates as verified by their subsequent e-receipt notifications. The present invention real-time payment authorization request and e-receipt notification process enables patients to 1) detect when their health care providers have circumvented the adjudication process, and insist on corrective action by health care providers; and 2) know the total payment due for the product or service, the amount, if any, paid on their behalf via their previously provided source of funding for such payments ("plan" payment) and the amount to be paid directly to the health care provider (patient "copay"), if any. The process of the present invention also significantly diminishes the potential for health care providers to unilaterally reverse claims because 1) if during the adjudication process, it is determined that there are sufficient funds available from the patient's source for full or partial payments, the healthcare claims processor pricing edits will convey to the provider that the "plan" will be paying for either a part or all of the adjudicated cost of the provider's product or service; and 2) the patient receives an e-receipt message notification indicating the health care provider has reversed a previously submitted claim enabling the patient to request the resubmission of the claim unless they agree with the reversal decision.

The present invention provides a significant deterrent for health care providers to attempt to "game" the system. Since all patients receive a payment e-receipt notification (typically in real-time, but at a time determined by the healthcare claims processor) indicating the correct, discounted price that either will be or should be paid to their health care provider every time a service or product is provided, and another e-receipt message notification when a health care provider reverses a claim, the present invention provides the means to consistently audit and prevent the occurrence of claim adjudication circumvention, a problem which all retrospective approaches have failed to accomplish to date.

Adjudication circumvention is an industry-wide deficiency for all healthcare (pharmacy, medical, etc.) claims. All HDHPs (including CDHPs) are 100% patient copay until the deductible is met; and they function exactly like cash discount programs, with the patient paying the entire cost of the product or service until deductibles are met. The significance of the problem is best summarized by the following: 1) under High Deductible health plans, more than half of all insured Americans spend less on health care during the course of any year than the total amount of their deductible; and 2) approximately ninety (90%) of all consumers never meet their deductible under Consumer Driven health plans. As the fastest growing segment of the health insurance industry, one can expect the growth of the problems identified herein to be commensurate in the absence of the present invention.

When it is easy to exploit a system for financial gain with very little chance of exposure and limited penalties, if any, when caught, it is logical to conclude a significant percentage of providers will take advantage of the opportunity. Without the present invention and the previous patent application, all healthcare claims processors are currently incapable of preventing health care providers from circumventing the claim adjudication process in all 100% copay situations (cash discount programs and HDHPs, particularly CDHPs—the fastest growing segment of the health insurance industry) at the point of service. This is an industry-wide deficiency that generates significant problems for patients, plans, and healthcare claims processors.

It is not uncommon for health care providers to use patients who are responsible for the full cost of their product or service to subsidize the managed care reimbursement rates that most health care providers perceive have been forced upon them. This is easily accomplished since health care providers can simply circumvent the adjudication process by unilaterally electing to not submit the claim or reversing the claim when it becomes apparent that patients will bear the full financial responsibility for provided products and services. Health care providers can then charge "what the market will bear", without the patient's, plan's, or healthcare claims processor's knowledge or consent. This provider behavior may not be consistent with the terms of their contract with either health plans or healthcare claims processors, but the repercussions, if any, in the rather unlikely event health care providers are caught, have not eliminated the problem to date.

Currently, there is no known approach being used by cash discount programs to prevent adjudication circumvention. Under cash discount programs there are two reasons for health care providers to engage in adjudication circumvention: 1) to secure a higher reimbursement rate from the patient than the previously agreed upon discounted contract rates; and 2) to avoid paying a fee that is assessed by healthcare processors associated with providing a product or service under their cash discount program for providing "steerage" to health care providers. Since the present invention prevents health care providers from circumventing the adjudication process under cash discount programs, it not only protects the patient but also increases the revenue healthcare claims processors receive.

Under traditional, fully funded healthcare plans which utilize a patient and health plan cost-sharing arrangement to pay for the total cost of a health care provider's service or product, health care providers are required to submit claims in order to receive the health plan's share of the total cost. During the claim adjudication process, edits sent back to the health care provider indicate the amount to be paid by each party. However, under plans and programs in which at some point, patients are responsible for the total cost (100% copay) of the service or product received (such as high deductible health plans before the deductible is met, and all cash discount card programs), health care providers have an opportunity to circumvent the claims adjudication process by simply intentionally by-passing the claims submission process or reversing a previously submitted claim and charging the patient "what the market will bear", with limited, if any, chance that their unilateral decision will be detected.

The significance of the problem in the pharmacy benefits sector alone is illustrated by the fact that it is not uncommon for cash discount programs to experience claim reversal rates ranging from twenty percent (20%) to fifty percent (50%), with those reversal rates ranging from four (4) to ten (10) times that experienced under traditional, fully funded pharmacy benefit plans when patients' (cost-sharing) copays alone are approximately the same amount as the average prescription cost under cash discount programs. Consequently, the cost of prescriptions cannot explain the difference in claim reversal rates. Under traditional prescription drug plans that utilize a cost-sharing copay structure, health care provider self-serving claim circumvention is not possible because health plans (insurers) are responsible for a share of the cost. Also, under Consumer Driven Health Plans, approximately ninety percent (90%) of plan members never meet their deductible and under traditional High Deductible Health Plans (HDHPs), approximately fifty percent (50%) of plan members never meet their deductible. This further reduces the potential for health care providers being caught; because before deductibles are met, patients in these plans experience the same vulnerability as they would under cash discount card programs. The only difference between HDHPs/CDHPs and cash discount cards is that HDHPs/CDHPs have a patient deductible that, once met, automatically converts to a cost-sharing arrangement with the health plan and this eliminates the problems.

The present invention eliminates the problem of claim submission circumvention and over-charging under all 100% patient copay situations via healthcare claims processor pricing edits to providers during the adjudication process and the e-receipt that is sent to the patient. The pricing edits indicate either 1) a 100% "plan" payment responsibility; 2) a patient (partial pay) and "plan" sharing responsibility; or 3) a 100% patient payment ("copay") responsibility, depending upon the real-time response to a healthcare claims processor's initiated payment authorization request indicating the availability of funds from the patient's previously provided source of funds for healthcare claims processor initiated payments to health care providers. Once the claim is adjudicated and the patient's funds payment capability is determined, the patient, or representative, is sent a claim payment e-receipt via the patient's preferred method (e-mail, text/SMS, voice/audio, fax, push notification via a mobile app, etc.) indicating 1) the adjudicated amount due for the service or product; 2) the amount to be paid from the patient's previously provide source for such "plan" payments, if any; and 3) the patient's responsibility for payment directly to the health care provider (patient "copay"), if any. The claim payment e-receipt verifies claim submission; and since it indicates the patient's payment responsibilities, the patient knows the exact amount, if any, for which they have direct payment (patient "copay") responsibility. Consequently, if an e-receipt is not received, the patient knows the claim was not submitted for adjudication and can address the issue with their health care provider. Also, patients receive a payment reversal e-receipt if the provider subsequently reverses their claim, thereby enabling the patient to address the need for the health care provider to resubmit the claim unless the patient agrees with the reversal decision.

The present invention eliminates healthcare claim adjudication circumvention and the resulting problems via healthcare claims processor's initiated action. When the present invention process is integrated into the healthcare claims processor's claim adjudication process, the healthcare claims processor initiates a patient's payment from a patient's previously provided source of funding (bank, credit card, etc.) via a payment authorization request to pay for the products and services they receive when the amount of funds in the patient's funding source is adequate for such payment rather than the patient making direct payment for their complete financial responsibility.

If a patient does not receive a payment e-receipt, the patient knows their claim has not been submitted for adjudication and can address this issue with their health care provider to force claim submission. Since a claim reversal is also a possibility, a claim payment reversal e-receipt indicating a claim reversal is sent to the patient (typically in real-time, but at a time determined by the healthcare claims processor) enabling the patient to request health care provider resubmission of the claim unless they approve the reversal. Reversals are a problem when the service or product is received, even when the e-receipt verified the adjudicated payment due is requested because that eliminates the pricing issue but not the other five problems that can be experienced when claim adjudication is circumvented. The present invention process functions are fully integrated within a healthcare claim processor's claims adjudication process and they eliminate the potential for experiencing each of the six problems noted below when claims are not adjudicated:

1. Patients paying more than the health plan's or healthcare claims processor's negotiated discount rates with their network health care providers for their products and services.
2. Claims not being counted toward patients' deductibles (when applicable)
3. Deductibles, if applicable, not being tracked at the point of service. This means that, if patients would hit their deductible with the service or product then being provided, they would not receive the benefit of a reduction in their financial responsibility at that time, with their third party (such as a health plan, etc.) picking up the difference, a difference which would require frustrating and expensive corrective action later if detected.
4. Patients not receiving concurrent Drug Utilization Review (DUR) on all prescriptions, thereby making them susceptible to drug therapy related problems that otherwise could have been avoided. Concurrent DUR is provided via healthcare claims processors' computerized programs that, before prescriptions are dispensed, electronically alert pharmacists to drug interactions, duplicate therapies, and other potential drug therapy related problems caused by taking two or more prescription drugs. Through DUR, the cost of therapy is controlled and becomes cost-effective because it reduces the need for other medical services, such as hospitalizations, nursing home admissions, and additional physician visits. It also decreases the potential for meeting patient deductibles, thereby minimizing the underwriting risk. Obviously, circumventing the adjudication process increases patients' risk not only for drug therapy related problems but also other healthcare problems.
5. Data required for accurate actuarial and clinical analysis, risk prediction, projected outcomes and optimal provider compensation under pay-for-performance (P4P), or value-based purchasing models are incomplete. Consequently, any results derived from available data would be inaccurate.
6. Healthcare claims processors losing the revenue that would be received by processing the circumvented claims.

The present invention requires a healthcare claims processor to integrate within their claims adjudication system a real-time process to initiate indirect patient payments to health care providers in all 100% copay situations and patient e-receipt message notifications (typically in real-time, but at a time determined by the healthcare claims processor) summarizing a patient's respective ("plan"/"copay") payment responsibilities. Upon determination of the adjudicated price, the healthcare claims processor will, in real-time, initiate a payment authorization request for patient funds from the patient's previously provided source of funding to enable full or partial "plan" payment of the adjudicated price for the product or service provided. Upon the real-time receipt of patient's funding source via the payment gateway/processor, the healthcare claims processor sends, in real-time, two pricing edits, as is the norm for fully funded plans, to the health care provider's computer system that indicate 1) in the patient's copay field, the amount of funds the health care provider should collect directly from the patient, if any; and 2) in the plan payment field, the amount of "plan" funds that will be paid to the health care provider from the patient's funding source (bank, credit card, etc.) via the present invention process.

The healthcare claim processor's integration of the present invention in their claims adjudication process provides for a real-time payment authorization request for patient funds for "plan" healthcare provider payment and the patient's payment and payment reversal e-receipts provide patients in an out-patient setting an ability to: 1) force claim submission when providers intentionally avoid it; 2) limit payment for their healthcare services and products to that as determined by the claims adjudication process rather than the provider's payment preference; and 3) require providers to re-submit any claim reversal that does not have the patient's approval, approval that is typically limited to clinical issues or a price that exceeds a patient's ability or willingness to pay.

Briefly, the present invention provides patients control of the claims adjudication process because it precludes health care provider self-serving claim adjudication circumvention, claim reversal actions, and pricing at "what the market will bear" rather than the healthcare claims processor's adjudicated discount rates.

At about the same time that the healthcare claims processor is sending the pricing edits to the health care provider, a payment e-receipt message notification is being sent to the patient by the payment gateway/processor (typically in real-time, but at a time determined by the healthcare claims processor) which indicates 1) the total adjudicated amount due; 2) the amount of the funds which will be paid to the health care provider on the patient's behalf from the patient's previously registered funding source ("plan" payment), if any; and 3) the amount that should be paid by the patient directly (patient "copay") at the point of service, if any. In the event a health care provider initiates a claim reversal, a claim payment reversal e-receipt message notification (typically in real-time, but at a time determined by the healthcare claims processor) is provided to the patient notifying the patient of the health care provider's actions, thereby enabling the patient to require claim resubmission if the patient does not agree with the reversal. The combination of a healthcare claims processor automatically initiating patient payments to pay health care providers on behalf of patients along with the patient's claim payment and claim payment reversal e-receipt message notifications pre-empts health care providers' ability to unilaterally circumvent the adjudication process and transfers control of the claim adjudication decision from health care providers to patients and healthcare claims processors.

The present invention's process for patient payment to health care providers for products and services from a patient provided funding source can be employed internally by healthcare claims processors or outsourced to one or more entities employing the processes to fulfill the various optional functions of the process in the present invention, a process which results in removing the patient's need to pay the health care provider directly for healthcare products or services. Once the price determination component of the healthcare claims adjudication process is completed, the process for which patent protection is being sought is: 1) during the claim adjudication process, the healthcare claims processor sending the adjudicated price, in real-time, to a payment gateway/processor via a payment authorization request that employs both a unique patient identifier and a secure payment token to the patient's preferred method or instrument of payment (debit/credit card, bank draft account, ACH, or other then current payment method consistent with industry standards) to process a payment transaction to secure the funds for the healthcare claims processor, or health plan, to subsequently provide payment to the health care provider on behalf of the patient; 2) upon a healthcare claims processor's real-time receipt of funds availability from the payment gateway/processor, the healthcare claims processor sends real-time pricing edits to the health care provider indicating how much, if any, should be collected directly from the patient (copay) and how much, if any, will be paid by the "plan"; 3) at about the same time, a payment e-receipt message notification is sent to the patient, or patient's representative (typically in real-time, but at a time determined by the healthcare claims processor), indicating: a) the adjudicated amount due; b) the amount of the patient's funds which were authorized for payment from the patient's source of funding for "plan" payments, if any, to the health care provider; c) the amount of funds, if any, for which direct patient payment is to be made (patient "copay"); and d) if applicable, a payment reversal e-receipt message notification to the patient indicating their health care provider reversed the previously submitted and adjudicated claim. The preceding enables the patient to 1) confirm that their claim was submitted and adjudicated; 2) be assured that they will always pay the health care provider the correct, adjudicated discount price; and 3) know that, since their claim was adjudicated, none of the six problems previously noted will be experienced.

The present invention provides a real-time quality control feature that is integrated within a healthcare claim processor's existing claims adjudication process. It removes the current vulnerability of patients because it provides assurance that patient claims will be submitted and adjudicated and the payments made to health care providers are the adjudicated amounts. The present invention eliminates the six previously noted problems that are experienced when healthcare providers circumvent claim adjudication; and via a claim payment reversal e-receipt, provides an audit of the claim reversal actions by health care providers to enable patients to force health care providers to resubmit the claim when they do not approve the claim reversal.

The present invention enables patients to 1) immediately detect that their health care providers have circumvented the adjudication process and probably charged "what the market will bear;" and 2) insist upon claim submission. The present invention also provides a significant deterrent for health care providers to attempt to "game" the system since they will be caught doing it. Since all patients receive a patient e-receipt message notification (typically in real-time, but at a time determined by the healthcare claims processor) indicating the correct, adjudicated price that should be paid to their health care provider every time a service or product is provided, the present invention provides the means to consistently prevent the occurrence of claim adjudication circumvention which retrospective approaches fail to accomplish.

Patients receive payment e-receipt message notifications of the adjudicated price that should be charged for the product or service received as well as the amount authorized for "plan and patient copay payments when health claims (including, but not limited to, medical, prescription/pharmacy, dental, vision, durable medical equipment, laboratory, etc.) have been adjudicated. Therefore, the absence of payment e-receipt message notifications to patients (typically in real-time, but at a time determined by the healthcare claims processor) indicates claims have not been adjudicated and this enables patients to force health care providers to submit claims for adjudication and charge them the correct adjudicated rates as specified by the healthcare claims processor's pricing edits. Additionally, patients receive subsequent claim payment reversal e-receipt message notifications when health care providers reverse claims that enables them to effectively address this issue. The preceding provides a shift in control of the claims adjudication process from health care providers to patients and healthcare claims processors by forcing health care providers to submit claims for adjudication. Health care providers' ability to unilaterally reverse claims or intentionally choose to not submit claims for adjudication is eliminated, as are all of the problems experienced when claims are not adjudicated. It also assures that reversals are limited to patient decisions such as the network discount price exceeding the patient's ability or desire to pay, etc.

The present invention eliminates inappropriate healthcare provider excess charges, enhances the quality of patient care by eliminating clinical problems, increases appropriate healthcare claims processor net revenue, decreases healthcare claims processor deductible related problems, and facilitates accurate actuarial and clinical analysis, risk prediction, projected outcomes and optimal provider compensation under pay-for-performance (P4P), or value-based purchasing models.

While this invention has been described as having preferred design, it is understood that it is capable of further modifications, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A computerized system for payment of a product or service provided by a health care provider to a patient with full financial responsibility (100% copay) and e-receipt notification for real-time prevention of healthcare claim adjudication circumvention, comprising:

a) healthcare provider computer for transmitting to a healthcare claims processor platform for claim adjudication of a claim transaction resulting from the patient receiving a service or product from the healthcare provider, the health care provider computer for receiving pricing edits from the healthcare claims processor platform of the claim transaction, the pricing edits including a copay amount and a plan pay amount;

b) electronic notification server for sending, via a preferred method of electronic notification of the patient, a claim payment e-receipt to the patient at about the same time as the pricing edits are sent to the healthcare provider computer, with the claim payment e-receipt indicating total amount and an amount debited from a funding source of the patient, with a difference, if any, being a copay to be paid by the patient directly to the health care provider, wherein failure for the patient to receive the claim payment e-receipt indicates that the health care provider has failed to submit the claim transaction for adjudication, thereby enabling the patient to request the healthcare provider to submit the claim transaction for adjudication;

c) first application server for registration of personal information and the funding source of the patient and the preferred method of electronic notification, the application server for assigning a patient's unique patient identifier and a unique payment token to the patient, a second application server of the healthcare claims processor for sending member eligibility information to the first application server containing the patient's unique patient identifier and unique payment token, the first application server for matching individuals identified in the member eligibility information with the corresponding patient's unique patient identifier and unique payment token, the first application server for sending the patient's unique patient identifier and unique payment token to the second application server of the healthcare claims processor, the first application server for sending a payment authorization request from the healthcare claims processor adjudication platform to the funding source through a payment gateway, with patient funds to be deposited in a designated bank account for subsequent payment to the health care provider, the first application server for sending notification received from the funding source through the payment gateway to the healthcare claims processor, the first application server for sending the claim payment e-receipt via the electronic notification server to the patient; and d) the healthcare claims processor adjudication platform for receiving and adjudicating the claim transaction from the healthcare provider for an adjudicated price to determine the patient's financial responsibility for the product or service, the healthcare claims processor platform for sending to the healthcare provider the copay amount and the plan pay amount based on the claim adjudication and patient funds availability from the funding source at about the same time as the patient receiving the claim payment e-receipt, whereby the patient is informed of its financial responsibility owed to the healthcare provider in real-time to prevent the healthcare provider from circumventing the claim adjudication.

2. The computerized system as in claim 1, and further comprising a web server operably connected to the internet, the web server for receiving the patient's personal information, including the patient's preferred method of electronic notification and funding source.

3. The computerized system as in claim 2, and further comprising a third party registration server for transmitting patients' registration information including each patient's personal information including the patient's preferred method of electronic notification and funding source to the web server.

* * * * *